United States Patent
Verheijen et al.

(10) Patent No.: US 7,361,485 B2
(45) Date of Patent: Apr. 22, 2008

(54) METHOD FOR THE DETECTION OF PROTEOLYTIC ENZYMES

(75) Inventors: Johan Hendrikus Verheijen, Berkel en Rodenrijs (NL); Jan Roeland Occo Hanemaaijer, Voorhout (NL)

(73) Assignee: Nederlandse Organisatie Voor Toegepast-Natuurwetenschappelijk Onderzoek Tno, Delft (NL)

( * ) Notice: Subject to any disclaimer, the term of this patent is extended or adjusted under 35 U.S.C. 154(b) by 0 days.

(21) Appl. No.: 10/543,735

(22) PCT Filed: Jan. 29, 2004

(86) PCT No.: PCT/NL2004/000067

§ 371 (c)(1),
(2), (4) Date: Dec. 30, 2005

(87) PCT Pub. No.: WO2004/067768

PCT Pub. Date: Aug. 12, 2004

(65) Prior Publication Data

US 2006/0240406 A1    Oct. 26, 2006

(30) Foreign Application Priority Data

Jan. 31, 2003    (EP) ................... 03075319

(51) Int. Cl.
*C12Q 1/37*  (2006.01)
*G01N 33/53*  (2006.01)
(52) U.S. Cl. .................. 435/23; 435/7.6; 435/7.91
(58) Field of Classification Search ............ None
See application file for complete search history.

(56) References Cited

U.S. PATENT DOCUMENTS 5,811,252 A * 9/1998 Verheijen .............. 435/23

FOREIGN PATENT DOCUMENTS

EP     0 691 409 A    1/1996

OTHER PUBLICATIONS

Vocero-Akbani et al. Killing HIV-Infected Cells by Transduction With an HIV Protease-Activated Caspase-3 Protein; Nature Medicine, vol. 5, No. 1 (1999) pp. 29-33.*
Fadeel et al. Induction of Apoptosis and Caspase Activiation in Cells Obtained From Familial Haemophagocytic Lymphohistiocytosis Patients; British Journal of Haematology, vol. 106 (1999) pp. 406-415.*
Gruninger-Leitch et al. Substrate and Inhibitor Profile of BACE (Beta-Secretase) and Comparison With Other Mammalian Aspartic Proteases; The Journal of Biological Chemistry, vol. 277, No. 7 (2002) pp. 4687-4693.*
Zhou et al. Activation of Pro-Caspase-7 by Serine Proteases Includes a Non-Canonical Specificity; Biochem. J., vol. 324 (1997) pp. 361-364.*
Verheijen, Jan H., et al.: "Modified proenzymes as artificial substrates for proteolytic enzymes: Colorimetric assay of bacterial collagenase and matrix metalloproteinase activity using modified pro-urokinase." Biochemical Journal, vol. 323, No. 3, 1997, pp. 603-609, XP008019534 (abstract).

* cited by examiner

*Primary Examiner*—Jon Weber
*Assistant Examiner*—Paul Martin
(74) *Attorney, Agent, or Firm*—Weingarten, Schurgin, Gagnebin & Lebovici LLP

(57) ABSTRACT

The present invention provides an improved protease assay in which the proteases are detected on basis of their capability to cleave a modified pro-caspase which will yield an activated caspase which can then further be detected. Also part of the invention are the modified pro-caspases and kits comprising said modified pro-caspases.

14 Claims, 16 Drawing Sheets

Fig. 7B

Figure 1:
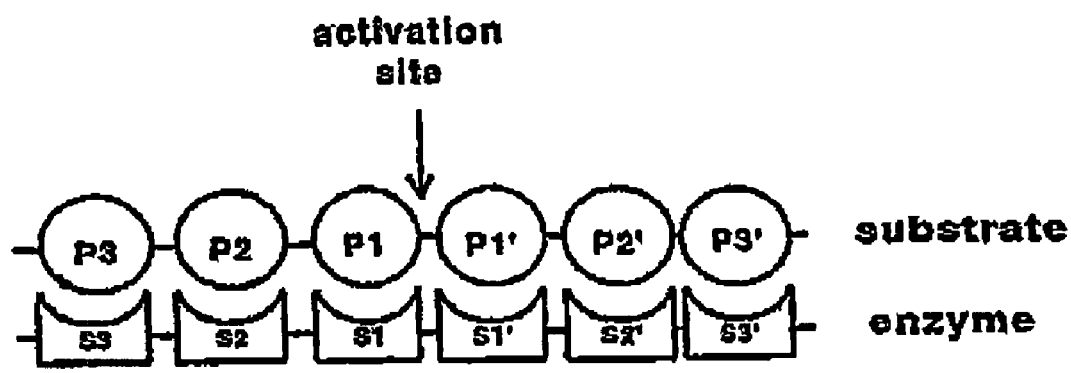

Oligos coding for activation site for target protein (here: TACE):

```
         P   L   A   Q   A   V   R   S   S   S   R
    ga tcc cca ttg gca cag gca gtt aga tct tca cgg g
       g ggt aac cgt gtc cgt caa tct aga agt agt gcc ctt aa
```

```
         G  I  E  T  G  S              E  F  S  G  V  D
      ggc att gag aca g              aa ttc agt ggt gtt gat
      ccg taa ctc tgt cct ag          g tca cca caa cta
```

BamH1    EcoR1

Qz expression vector cut with BamH1 and EcoR1

Ligation

| | EcoRbits | PLAQA VRSSSR | |
|---|---|---|---|
| Pro | Large subunit | Target protein Activation site | Small subunit |

Qz TACE expression vector

Fig 11 Time and concentration dependence of TACE activity assay

METHOD FOR THE DETECTION OF PROTEOLYTIC ENZYMES

This application is a §371 national phase filing of PCT/NL2004/000067 filed Jan. 29, 2004, and claims priority to a European application No. EP 03075319.8 filed Jan. 31, 2003.

The invention is in the field of determining or quantifying the activity of a proteolytic enzyme in a sample and concerns substrates, to be used therefore and an assay process and an assay kit and device therefore.

Proteolytic enzymes or proteases catalyze the hydrolysis of peptide bonds in proteins or peptides. These enzymes widely occur in nature from viruses to man and have many different functions. They are involved in digestive processes both on the level of the organism (digestive tract enzymes e.g. trypsin, chymotrypsin and pepsin) and individual cells (lysosomal enzymes e.g. cathepsins).

They play a role in migration and invasion of both micro-organisms and cells in multicellular organisms. In the latter they are involved in growth and development (e.g. plasmin, plasminogen activators and matrix metalloproteases). Besides these obvious degradation processes proteolytic enzymes play critical roles in regulatory networks such as blood coagulation, fibrinolysis, blood pressure regulation and pro hormone and growth factor processing. More recently it has been discovered that proteases play critical roles in cellular signalling and programmed cell death (apoptosis). Apart from these (patho) physiological functions proteolytic enzymes are increasingly used in biotechnology, ranging from e.g. pharmaceutical synthesis to preparation of food (e.g. cheese) and in very large scale in detergents for general and special use. Proteases can be used as pharmaceuticals themselves (e.g. plasminogen activators as thrombolytic agents) or be the target for drugs (e.g. HIV protease and angiotensin converting enzyme).

All proteolytic enzymes catalyze the same basic reaction:

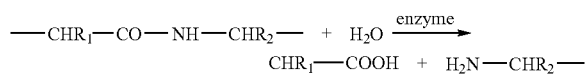

i.e. a peptide bond is hydrolysed under mild conditions, typically pH between 5-8 and temperature between 25-40° C. Without enzyme much harsher conditions such as boiling in 6 M hydrochloric acid are required. The difference between enzymatic and non-enzymatic hydrolysis of peptide bonds is not only a matter of conditions, enzymatic processes can be much faster and generally are much more selective than non-enzymatic hydrolysis.

Examples are known in which only one specific protein within a mixture is hydrolysed and sometimes only one specific peptide bond within one such a protein is attacked. The general mechanism behind this enormous improvement in efficiency and selectivity is that an enzyme contains an active site typically involving 2-3 amino acid residues directly involved in the catalytic step, as well as additional often more extended substrate recognition sites contributing to substrate or peptide bond recognition thus conferring specificity to the enzyme.

The known proteolytic enzymes can almost all be classified in four different classes based on the catalytic mechanism and the amino acid residues involved in catalysis (table I).

Within each class enzymes having different substrate specificities and properties occur. Many proteolytic enzymes are synthesised in an inactive, pro-enzyme or zymogen form. Activation, conversion of the inactive pro-enzyme form to the active proteolytic enzyme, is in most cases itself a proteolytic process. In this way positive or negative feedback regulation can occur, which is essential for proteolytic cascades like the ones occurring in blood coagulation and apoptosis.

Due to their involvement in many (patho) physiological processes, proteolytic enzymes play a role in many diseases and measurement of the activity of certain proteolytic enzymes can be important for diagnosis, prognosis or to follow therapy (see Table II). The use of compounds interfering with protease activity as drugs in a variety of diseases is increasing (e.g. anti-coagulants, HIV drugs).

Activity measurements of clinically important proteolytic enzymes are in general use. Especially for a number of key enzymes involved in the coagulation and fibrinolysis cascades, assays are used daily in clinical practice.

Measurement of activity of a protease using its natural substrate is not always possible, or leads to elaborate, complicated or non-specific assays not suitable for routine application. The development of peptide synthesis has led to the use of synthetic peptide (derivatives) as substrates for proteolytic enzymes. Especially for many serine proteases chromogenic or fluorogenic peptide substrates have been developed. These substrates are often commercially available and form the basis of complete assay kits. Development of such substrates for serine proteases is relatively easy since these enzymes do not recognize the sequence that is C-terminal to the bond to be hydrolysed. This C-terminal part can be replaced by a chromogenic or fluorogenic leaving group like p-nitro-aniline (pNA), β-naphtylamine (BNA), amino methyl coumarine (AMC) or 7-amino-4-trifluoro methyl coumarine (AFC). Upon this principle many commercially available substrates and assay kits are based and assays involving these methods can readily be automated.

In many cases the specificity and sensitivity obtained with these peptide substrates is sufficient to enable detection and quantification of physiologically relevant concentrations of proteolytic enzymes in biological fluids or tissue extracts. Sometimes the sensitivity can be further increased by employing two coupled reactions as has been described for plasminogen activators (Drapier et al. (1979) Biochimie 61, 463-471). Similar methods can also be used for measurement of activity of cysteine proteases. In recent years many peptide substrates have been developed for the caspase family of cysteine proteases involved in apoptosis.

Measurement of the activity of metalloproteases and aspartic proteases is more difficult. These enzymes, unlike serine- and cysteine-proteases do recognize the aminoacid sequence on both sides of the bond to be split (P3-P2-P1^P1'-P2'-P3') (FIG. 1).

Accordingly substrates where a non-peptide bond is split, such as the chromogenic or fluorogenic substrates used for determination of serine- or cysteine-proteases cannot be employed for determination of metalloproteases or aspartyl proteases.

Three different types of synthetic peptide substrates exist presently to be used for measurement of these enzymes: (1) peptides containing only the necessary recognition sequence for the protease. In this case hydrolysis is followed by physico-chemical techniques like HPLC or mass spectrometry; (2) Peptides containing a sulphur containing peptide bond equivalent on the hydrolysis site. The subsequent liberation of a thiolate group is monitored by a color reagent;

(3) Peptides containing besides the recognition sequence also a potential fluorescent group together with a quenching group. When both groups are in close proximity fluorescence is quenched. After hydrolysis of the cleavable peptide bond fluorescent group and quencher become separated and fluorescence is observed. Assays based on principle (1) are generally elaborate, difficult to set up, require special skills and equipment, are difficult to automate and cannot easily be run in a kinetic fashion. Assays based on principles (2) and (3) are in use but have a limited sensitivity and specificity.

Figure 2:
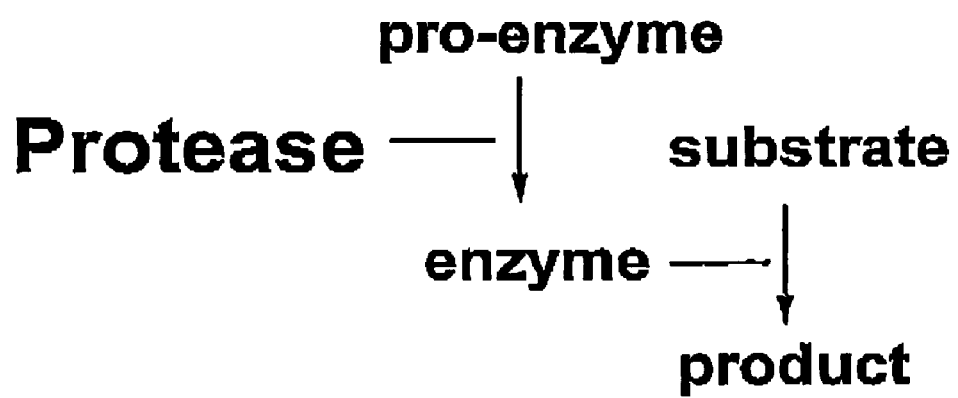

Some years ago a novel principle to detect protease activity was developed (see EP 691 409). In this principle a pro-enzyme is used that is modified in such a way that its normal activation recognition sequence is replaced or adapted in such a way that it can be cleaved by a protease of choice. Cleavage of this sequence results in an active enzyme that can be detected using conventional substrates (FIG. 2). Very suitable pro-enzymes for this principle are pro-enzymes of the serine protease family and particularly pro-urokinase. Based on pro-urokinase as a pro-enzyme, assays have been developed for many matrix-metalloproteases (MMPs), Granzyme B, various Cathepsins etc. Due to the involvement of a two stage reaction very sensitive assays have been developed measuring in the ng/ml or even pg/ml level. The first set of pro-urokinase based substrates was obtained by replacing typically 4 amino-acid residues N-terminal to the activation site by a 4 residue recognition sequence recognizable and cleavable by the target protease. This approach worked well for many proteases such as MMPs, Granzyme B and Cathepsins.

Figure 3A:
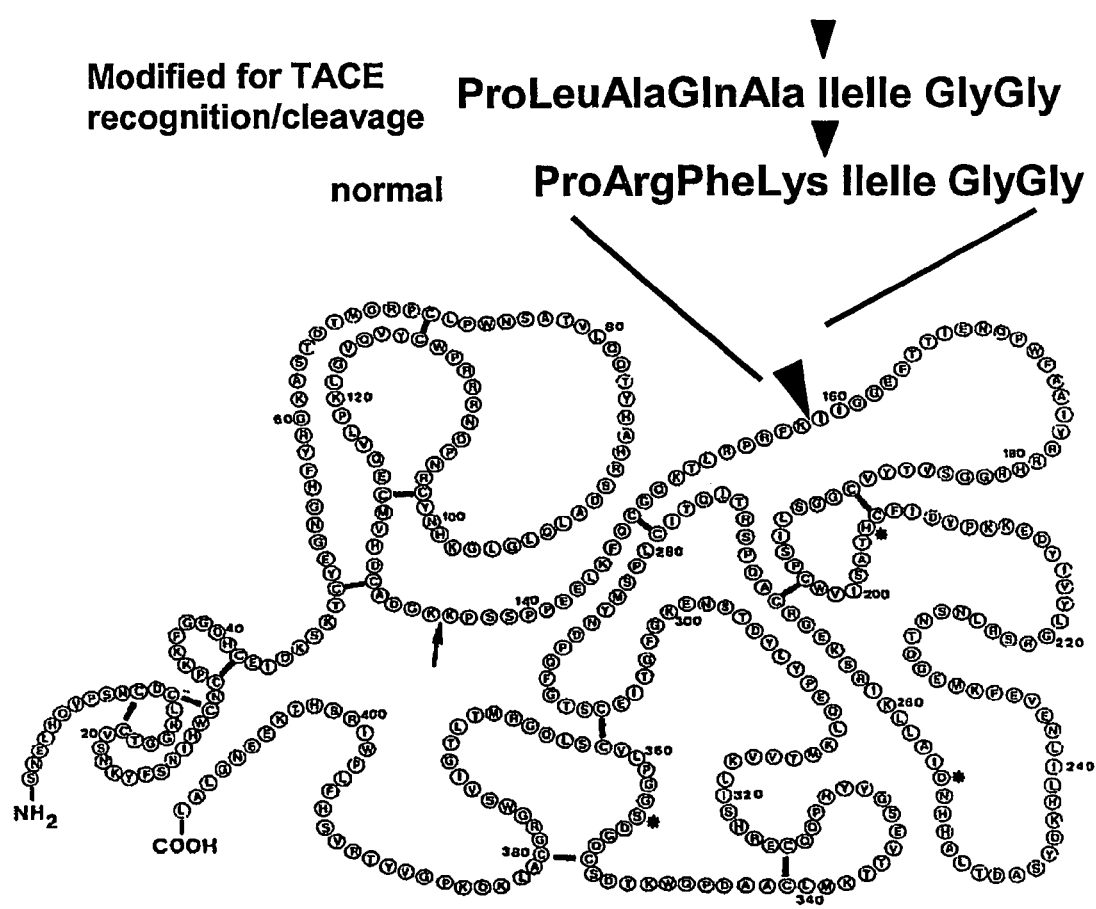
Figure 3B:
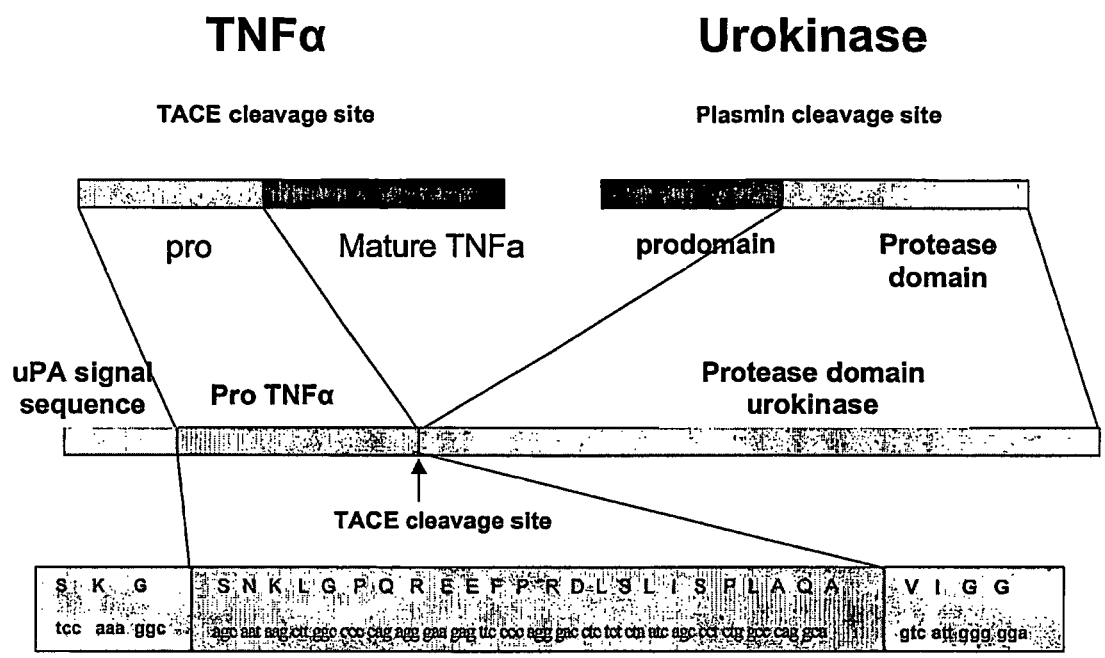
Figure 3C:
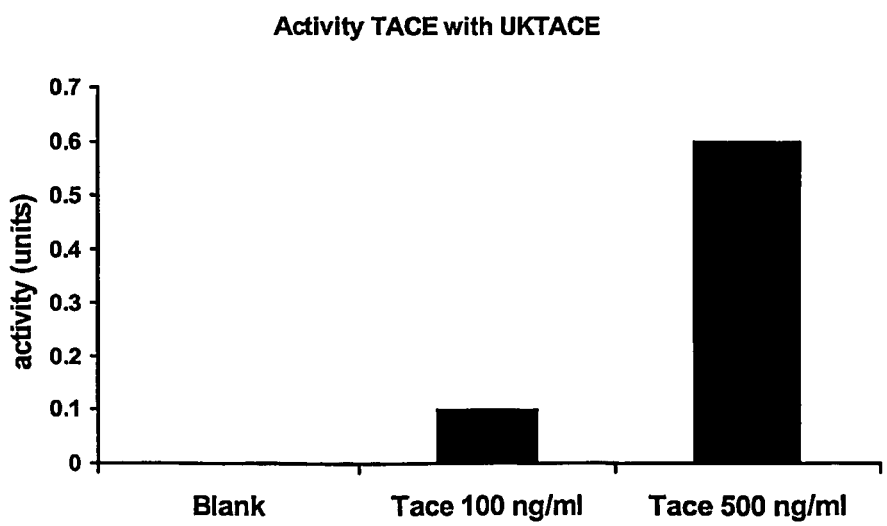
Figure 4A:
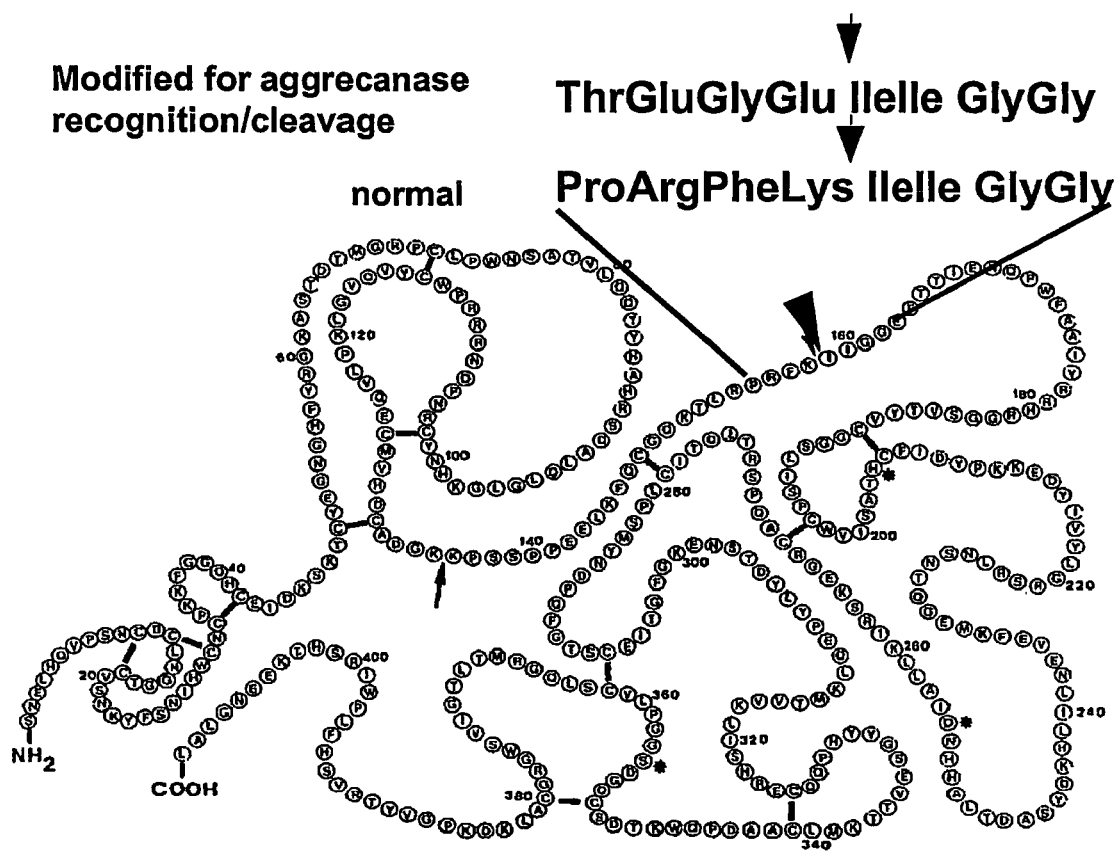
Figure 4B:
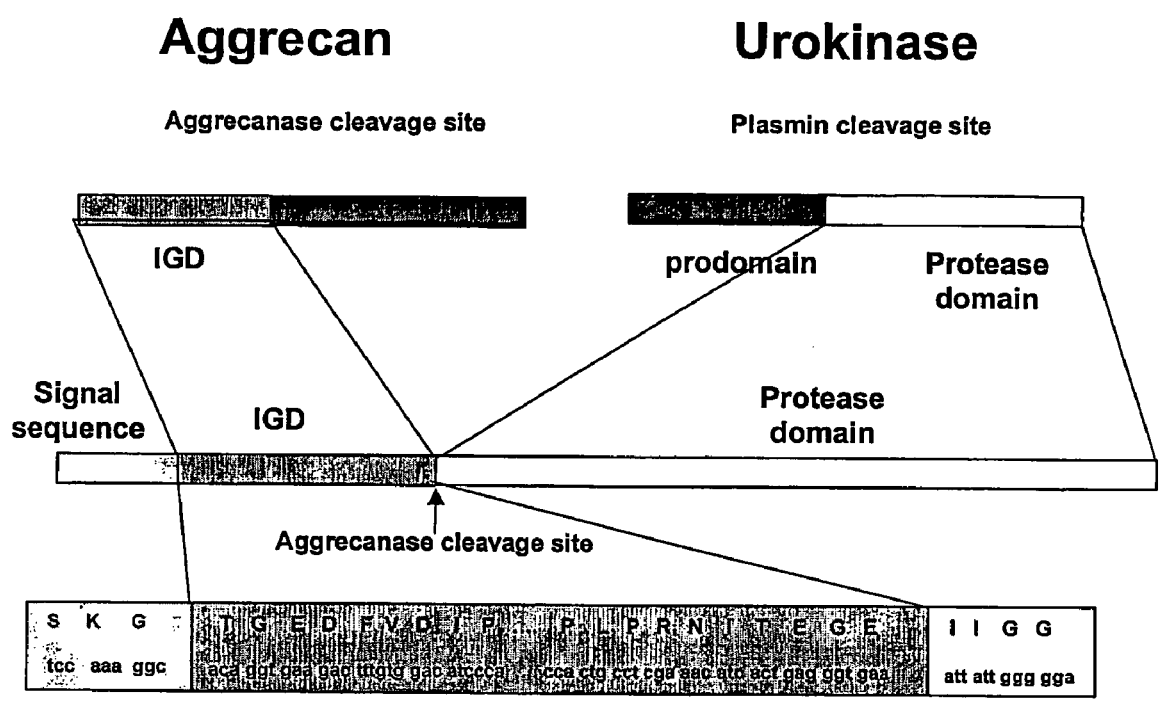
Figure 4C:
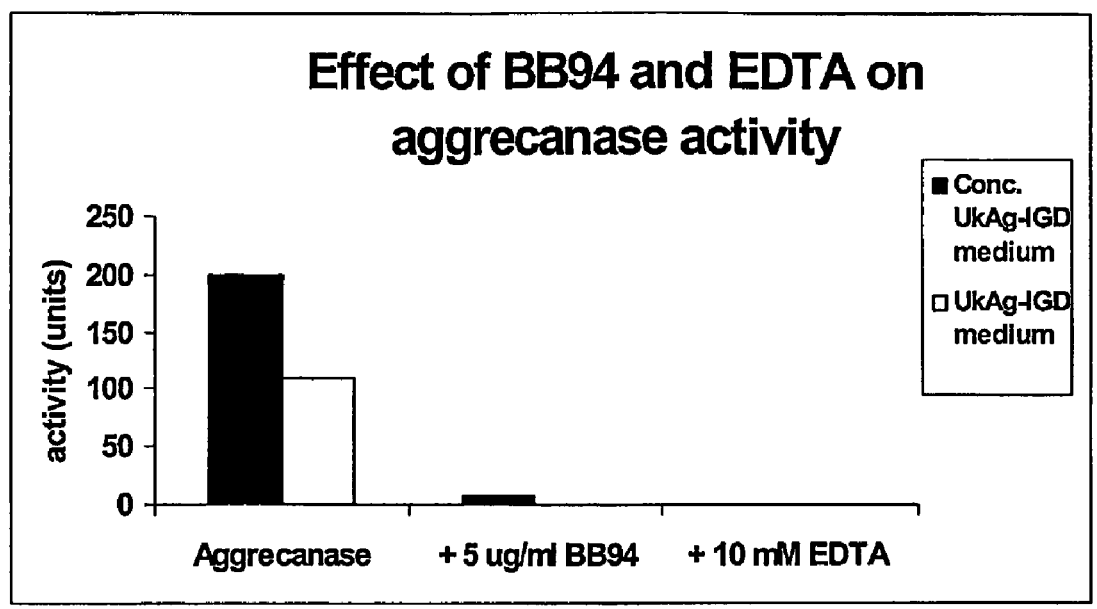
Figure 4C:
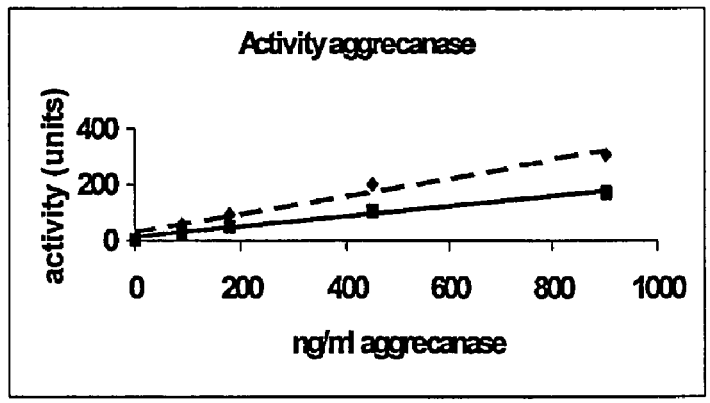

For some enzymes such as TNFα converting enzyme TACE (ADAM-17) and aggrecanase (ADAM TS4) this approach (FIG. 3a, 4a) resulted in very inefficient substrates. Much better substrates could be obtained by introduction of a longer recognition sequence. Introduction of a complete domain from the natural domain substrate N-terminal to the pro-urokinase activation site (FIG. 3b, 4b) resulted in much better pro-urokinase substrates. This approach resulted in relatively efficient substrates for aggrecanase (ADAM TS4) and TNFα converting enzyme TACE (ADAM-17) (FIG. 3c, 4c).

The use of serine proteases as detection enzyme has certain advantages such as easy detection of the activated enzyme, stability of the pro-enzyme and the availability of many possible candidate enzymes enabling optimization for special purposes. One major limitation was discovered, the amino acid sequence in the C-terminal part of the cleavage site cannot be chosen freely but has limitations based on structural and mechanistic constraints tightly linked to the serine proteases. Due to these limitations the development of efficient substrates for a number of interesting proteases proved elusive. In the present invention we describe a major improvement of the modified pro-enzyme technology not limited by the constraints typical of serine proteases and in principle enabling the development of substrates for any target protease.

The invention provides an improved method of determining a protease, or its precursor after activation, comprising incubating a sample with a target of said protease, determining proteolytic cleavage of said target, and correlating data obtained therefrom in order to determine the protease, wherein said target is a modified pro-caspase containing an activation site which is cleavable by said protease. The proteolytic cleavage of said modified pro-caspase activates the pro-caspase and the resulting activity is determined using a suitable substrate of the activated pro-caspase.

The sample can be selected from the group consisting of a biological fluid, a fraction thereof, a biological tissue, an extract thereof, a fraction of said extract, a culture medium conditioned by in vitro or in vivo growing cells, tissues, or organisms, an extract of such a culture medium, and a fraction of such a culture medium. The organisms and/or cells can be of any origin, such as viruses, bacteria, fungi (including yeast) and animals. The invention is very well applicable with samples derived from mammalians, especially humans, e.g. from body fluids or cell extracts.

The protease to be assayed can be any protease, but preferably the protease is selected from the group consisting of serine proteases, cysteine proteases, aspartyl proteases and metalloproteases and more preferably it is selected from the group consisting of aggrecanase (ADAM TS4), ADAM TS1, TACE (ADAM-17), BACE 1, BACE-2, HIV protease and hepatitis C protease. A non-exhaustive summary of proteases that could be possibly interesting to measure can be found in Table II.

The modified pro-caspase can be derived from a pro-caspase by replacing its activation site by an activation site which is cleavable by the protease to be determined, such as by removing its activation site and inserting, not necessarily on the same position, an activation site which is cleavable by the protease to be determined. Alternatively, the modified pro-caspase is derived from pro-caspase by altering its activation site rendering it inactive for its natural substrate and inserting, not necessarily on the same position, an activation site which is cleavable by the protease to be determined.

The modified pro-caspase is preferably selected from the group consisting of pro-caspase-1, pro-caspase-3, pro-caspase-7, pro-caspase-8, pro-caspase-9, and pro-caspase-10.

One embodiment of the invention which is particularly useful is a method wherein said modified pro-caspase is pro-caspase-3 or pro-caspase-7 and wherein said modification in pro-caspase-3 or pro-caspase-7 is a replacement of D175 in wild-type pro-caspase-3 or D198 in wild-type pro-caspase-7 by a sequence selected from the group of sequences similar to the aggrecanase recognition sequence from aggrecan (GSDMELPLPRNITEGE^ARGSVILTVK-PIFEEF) (SEQ ID NO: 1), the TACE recognition sequence from TNFα(GSPLAQA^VRSSSRSG) (SEQ ID NO: 2) or the BACE recognition sequence from β-amyloid precursor protein (GSKTEEISEVNL^DAEFRHDS) (SEQ ID NO: 3) where the ^ symbol indicates the cleavage site in the physiological target.

The caspase substrate is a compound which comprises an amino acid sequence which is cleavable by caspase and which further has a part that can be easily detected after cleavage. Examples of such substrates are summarized in Table IV and sequences of some known caspase substrates are shown in Table V. Preferably used is a compound comprising the amino acid sequence AspGluValAsp-pNA (SEQ ID NO: 4), in which pNA is p-nitro-anilide.

The invention also provides the modified pro-caspase per se, more particularly a modified pro-caspase derived from a pro-caspase by replacing its natural activation site or replacing an amino acid sequence in the region of its natural activation site by a modified activation site which is cleavable by a protease different from the one which activates the unmodified pro-caspase, or alternatively to insert such a modified activation site in the natural sequence of the pro-caspase.

Preferably, the modified pro-caspase is derived from pro-caspase-3 or pro-caspase-7.

The invention further provides a kit for determining a protease, or its precursor after activation, in a sample, comprising a modified pro-caspase as defined herein, together with the normal constituents of such a kit, such as substrates for activated pro-caspase, buffer solutions, standard preparations, detergents, specific antibodies, microtiterplates and instructions for use. In another embodiment, the invention provides a device for determining a protease or its precursor after activation, in a sample, comprising a modified pro-caspase as defined herein.

LEGENDS TO THE FIGURES

FIG. 1. Schematic illustration of the concept of substrate recognition by proteases in general; the proteolytic enzyme responsible for conversion of the substrate comprises amino acid residues s3, s2, s1, s1', s2' and s3', which, in the example shown, are involved in recognition of the amino acid residues P3, P, P1, P1', P2' and P3', which form the cleavage recognition site of the substrate; protease action results in cleavage of the peptide bond between residues P1 and P1'.

FIG. 2. Schematic illustration of the principle of the protease assay. The protease to be determined converts a pro-enzyme to an active enzyme. The active enzyme is subsequently measured by conversion of a substrate to a detectable product. The pro-enzyme conversion reaction and substrate conversion (detection) reaction can be performed simultaneously in one incubation step or be performed in two subsequent incubations.

FIG. 3. A. Structure of a modified pro-urokinase target substrate with a short recognition and activation site for TNFαconverting enzyme (TACE). The amino acid sequence shown in the figure is SEQ ID NO: 77.

B. Construction and structure of a modified pro-urokinase with an extended TNFαconverting enzyme (TACE) recognition and cleavage site based on a complete domain of TNFα. Residues 5-158 from pro-urokinase were replaced by residues 57-76 from pre pro TNFα. The amino acid sequence shown in the figure is SEQ ID NO: 79. The nucleotide sequence shown is SEQ ID NO: 78.

C. Demonstration of TACE detection using the modified pro-urokinase with extended TACE recognition site. Culture medium (100 μl) containing approximately 0.6 μg/ml of modified pro-urokinase as described in FIG. 3B was incubated on a microtiter plate coated with anti-urokinase antibody for 2-24 hr at 4-37° C. Subsequently the plate was washed and 0.8 mM of the urokinase substrate pyroGlu-Gly-Arg-pNA in 100 μl 50 mM Tris HCl pH 7.6, 1.5 mM NaCl, 0.5 mM $CaCl_2$, 1M $ZnCl_2$ and purified TACE as indicated was added. Absorbance was measured at 405 nm after various incubation times at 37° C. Activity was expressed as $1000*\Delta A_{405}$ divided by the square of the incubation time in hours.

FIG. 4. A. Structure of a modified pro-urokinase with a short recognition site for aggrecanase (ADAMTS4). The amino acid sequence shown in the figure is SEQ ID NO: 77.

B. Construction and structure of a modified pro-urokinase with an extended aggrecanase (ADANTS4) recognition and cleavage site based on a complete IgD domain of aggrecan. Residues 1-158 from pro-urokinase were replaced by residues 350-392 from aggrecan. The amino acid sequence shown in the figure is SEQ ID NO: 81; and the nucleotide sequence shown is SEQ ID NO: 80.

C. Detection of aggrecanase using the modified pro-urokinase with extended aggrecanase recognition site. Reaction conditions as described in FIG. 3C, wherein either approximately 3 μg/ml (solid line, black bars) or 30 μg/ml (dotted line, open bars) of modified pro-urokinase was used. Aggrecanase activity could be inhibited by the chelating agent EDTA and the specific metalloprotease inhibitor Batimastat (BB94) (Brown P. D., 1994, Clinical trials of a low molecular weight matrix metalloproteinase inhibitor in cancer, Ann NY Acad Sci. 6; 732:217-21).

Figure 5:
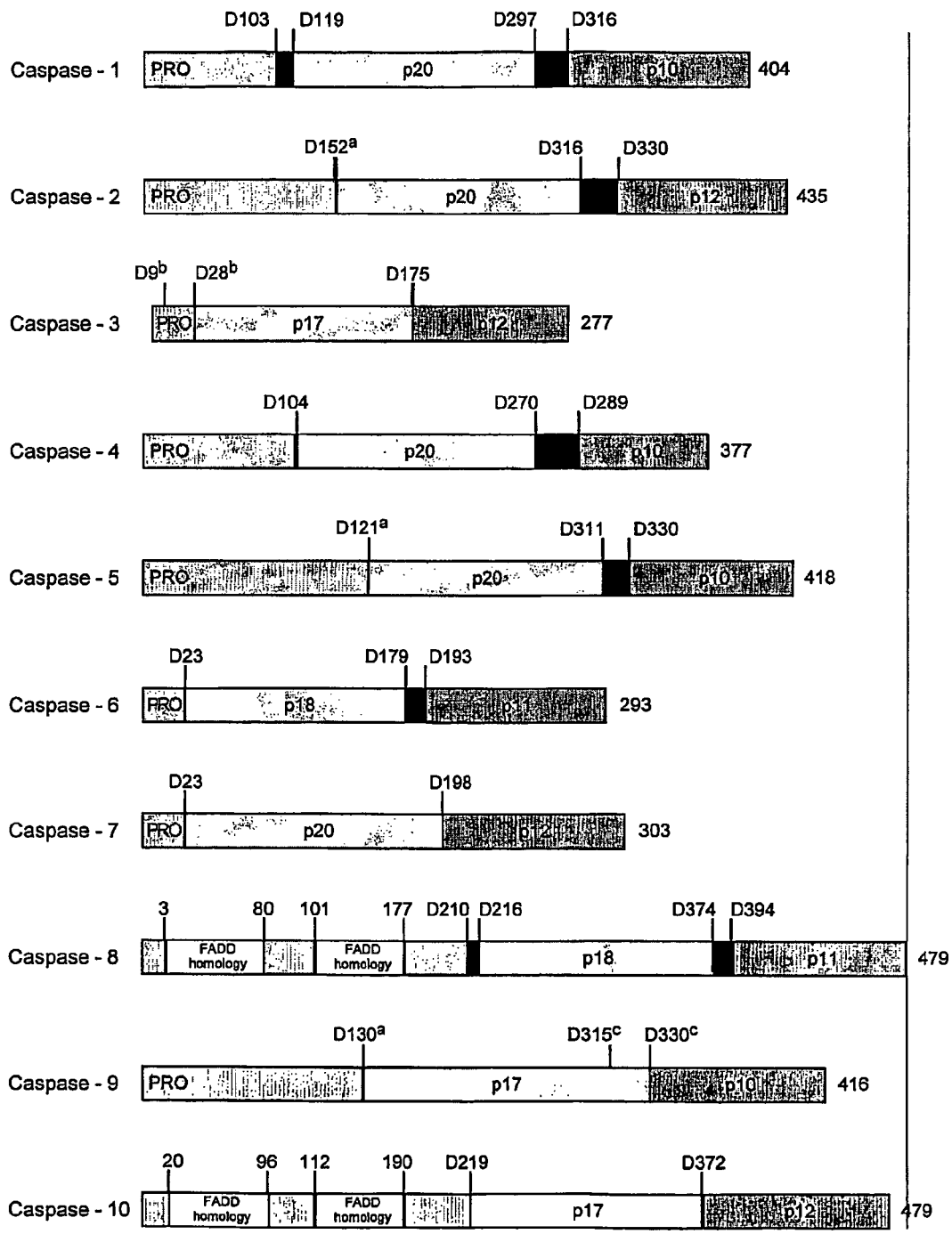

FIG. 5. Schematic overview of structure of pro-caspases. Pro-caspases are single chain polypeptides consisting of a pro-domain, a large subunit, a linker and a small subunit. The critical step that leads to activation is dimerization, which can be initiated by cleavage in the linker region. Cleavage of the pro-domain seems to be less essential. Linker regions vary in size between the different pro-caspases and can be as short as one residue in length. Cleavage sites that lead to activation are themselves cleavable by caspases. This results in a cascade of activation reactions. Auto-activation frequently occurs. The figure is from Cohen, G.M., Biochem J. (1997) 326, 1-16.

Figure 6:
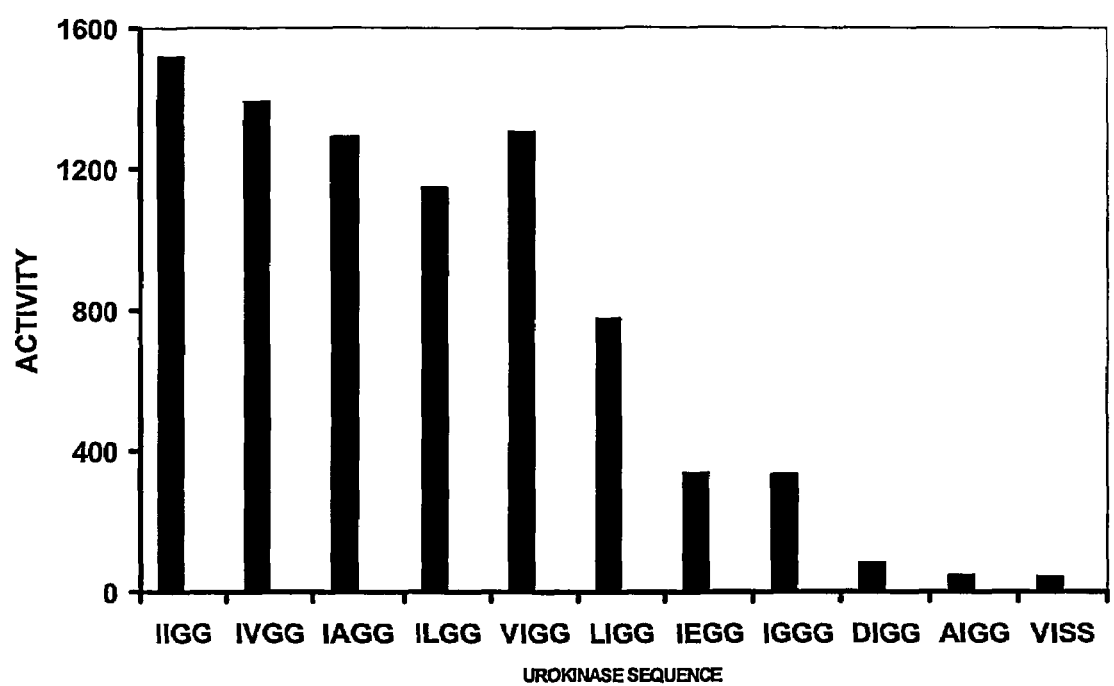

FIG. 6. Activity of mutant urokinase preparations with a variety of sequences C-terminal to the activation sequence. The peptides shown in the figure are IIGG (SEQ ID NO: 82), IVGG (SEQ ID NO: 83), IAGG (SEQ ID NO: 84), ILGG (SEQ ID NO: 85), VIGG (SEQ ID NO: 86), LIGG (SEQ ID NO: 87), IEGG (SEQ ID NO: 88), IGGG (SEQ ID NO: 89), DIGG (SEQ ID NO: 90), AIGG (SEQ ID NO: 91) and VISS (SEQ ID NO: 92).

Figure 7A:
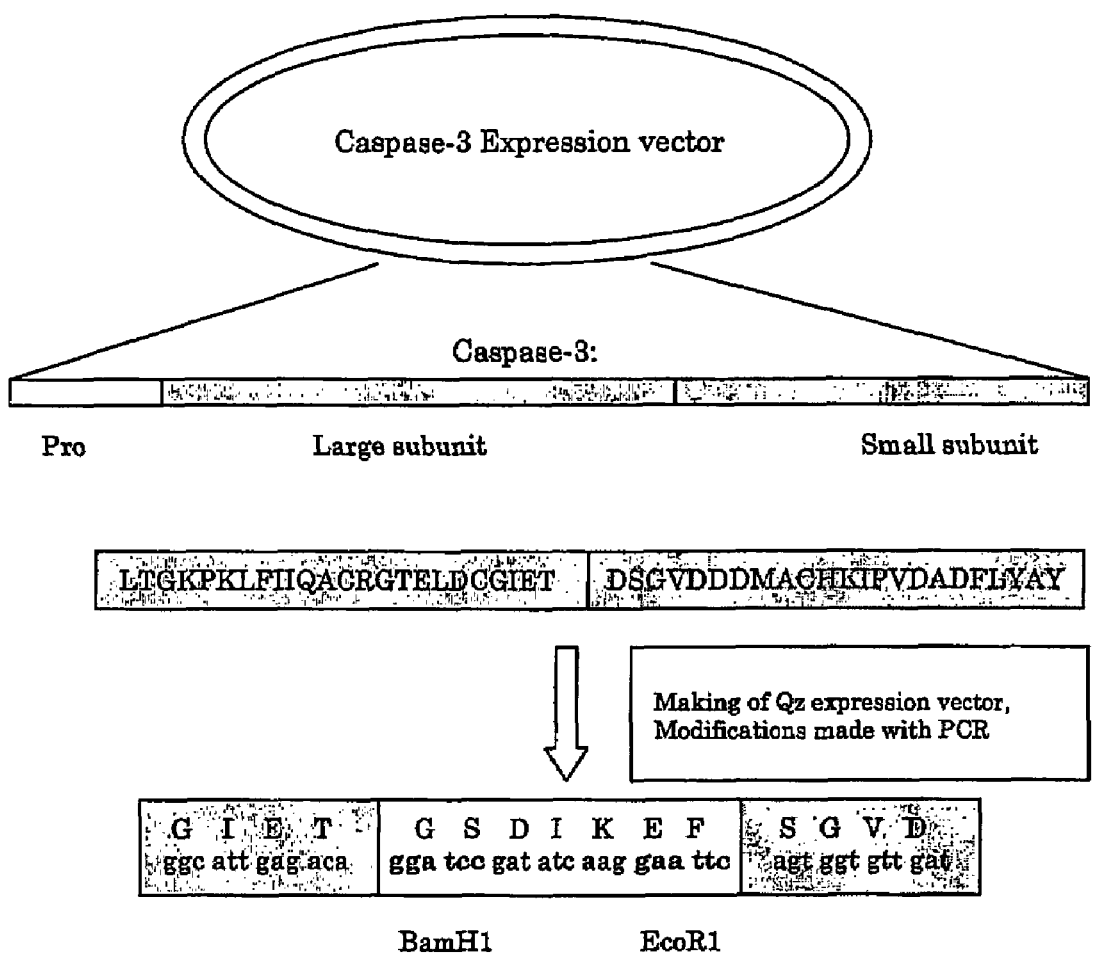

FIG. 7. A. Construction of a cassette expression vector for easy construction and expression of modified pro-caspase-3 molecules. The upper amino acid sequence shown in FIG. 7A is SEQ ID NO: 93. The lower amino acid sequence shown in the figure is SEQ ID NO: 95. The nucleotide sequence shown is in the figure is SEQ ID NO: 94.

B. Construction of an expression vector for modified pro-caspase-3 with a recognition/cleavage site for TACE using the cassette vector of FIG. 7A and a set of specific oligonucleotide linkers. The amino acid sequence shown in FIG. 7B is SEQ ID NO: 97; and the nucleotide sequence shown in the figure is SEQ ID NO: 96.

Figure 8:
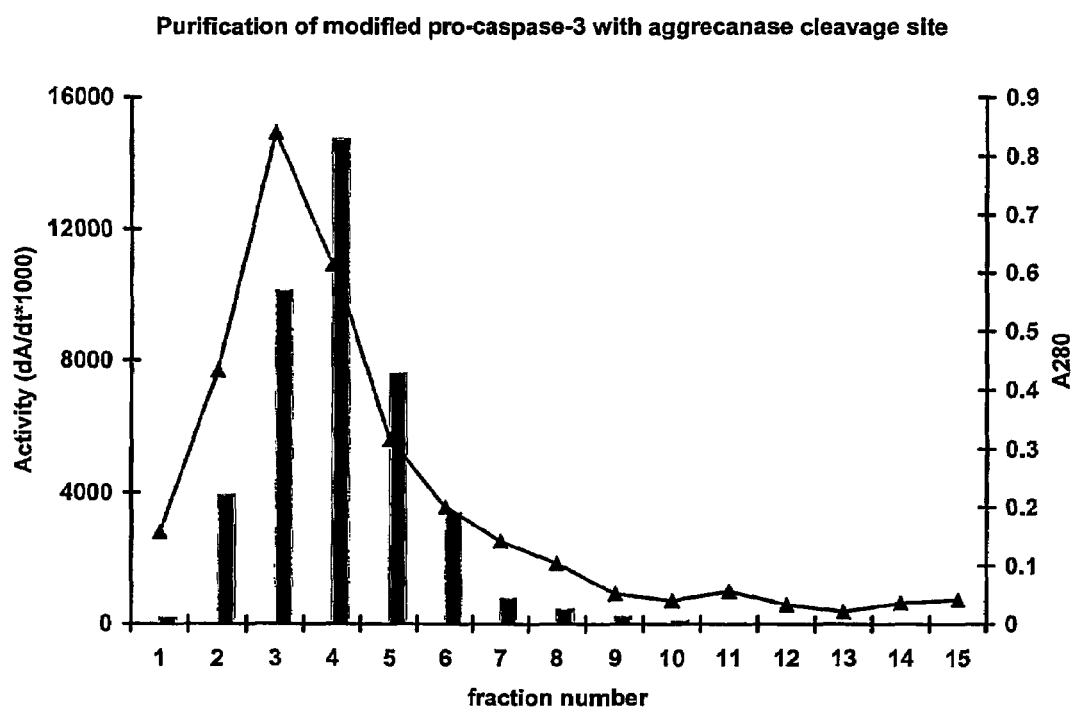

FIG. 8. Purification of bacterial expressed modified pro-caspase-3 on a Ni-chelate column.

Figure 9:
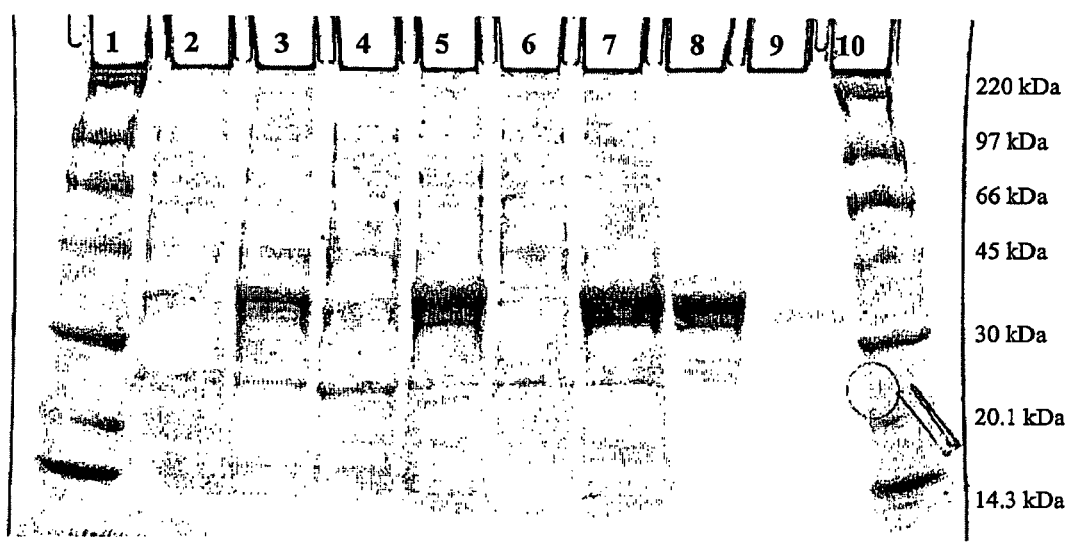

FIG. 9. SDS PAGE of bacterial extracts and purified fractions of modified versions of pro-caspase-3 and pro-caspase-7. Lane 1 and lane 10 contain a molecular weight marker (Rainbow marker, Amersham Biosciences), lane 2-8 are extracts from bacteria transformed with an expression plasmid coding for a modified pro-caspase-7 with an activation sequence recognizable by TACE, here indicated as Qz7.2TACE (see Example 3) harvested at 90 minutes (lanes 2, 3), 180 minutes (lanes 4, 5), and 270 minutes (lanes 6, 7) without (lanes 2, 4, 6) or with (lanes 3, 5, 7) IPTG. Lane 9 is control extract of strain Qz3 expressing unmodified wild-type pro-caspase-3 at 45 minutes+IPTG, after purification on a Ni-chelate column.

Figure 10A:
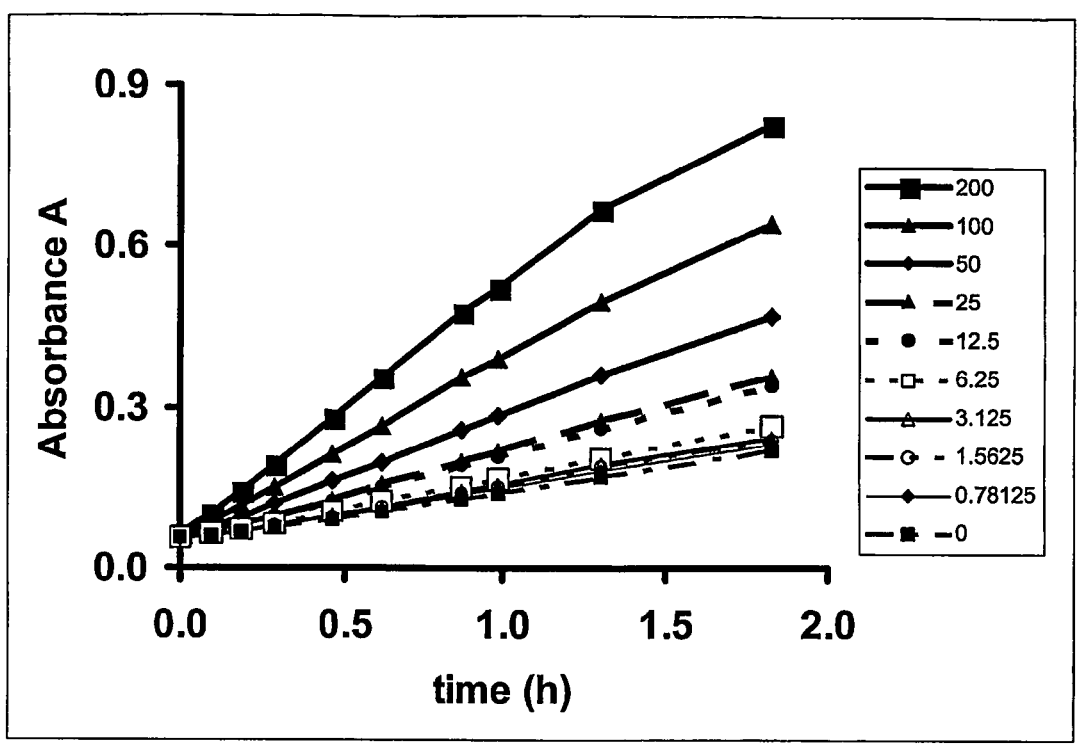
Figure 10B:
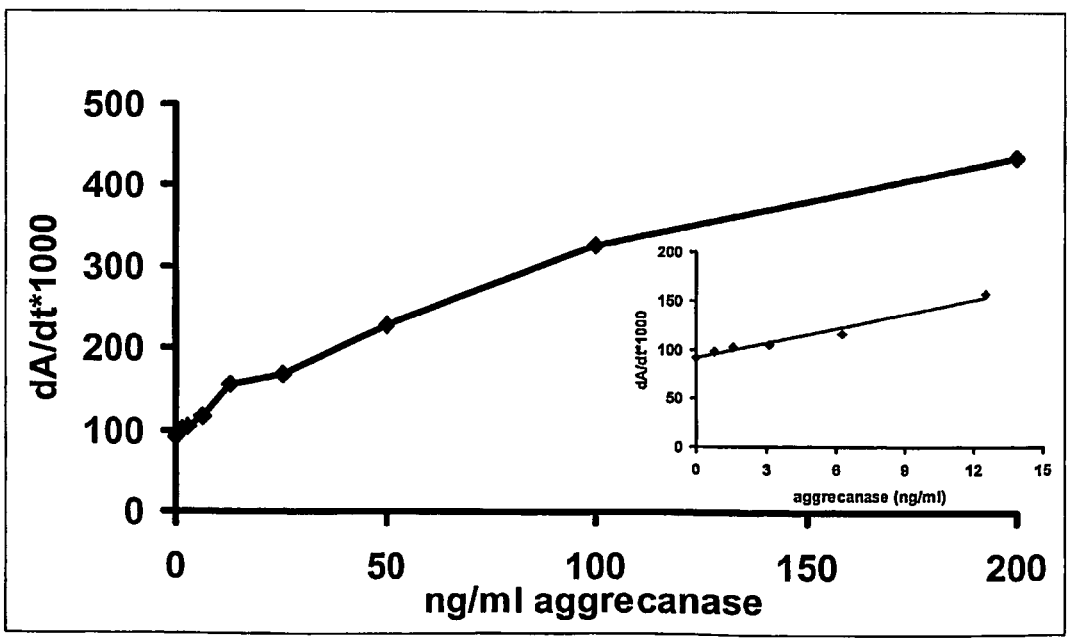
Figure 11A:
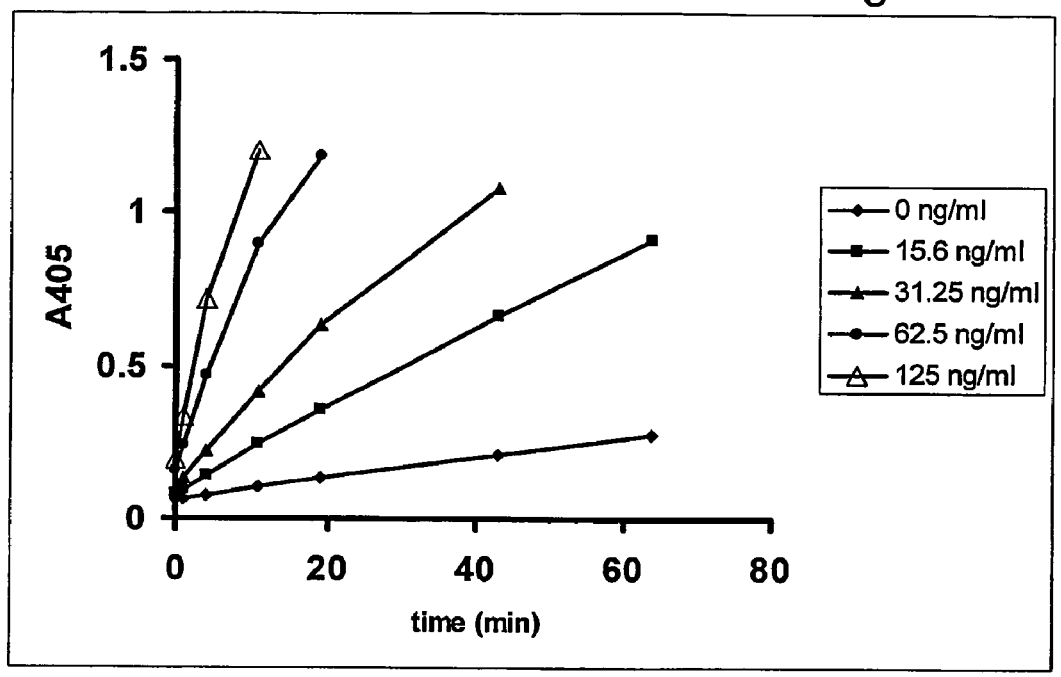
Figure 11B:
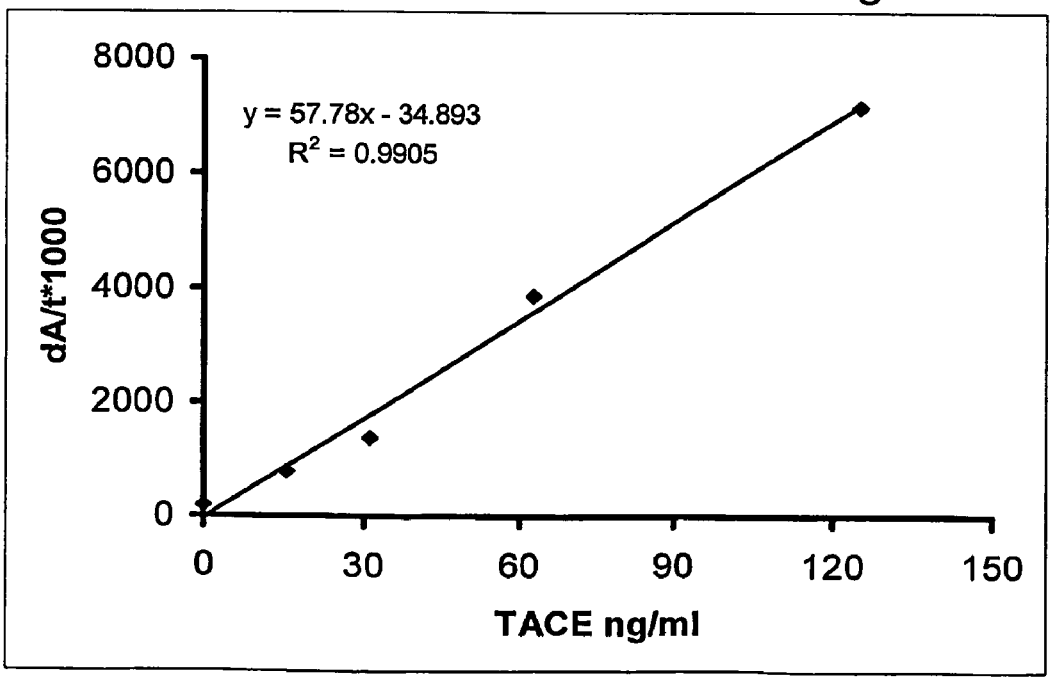
Figure 12A:
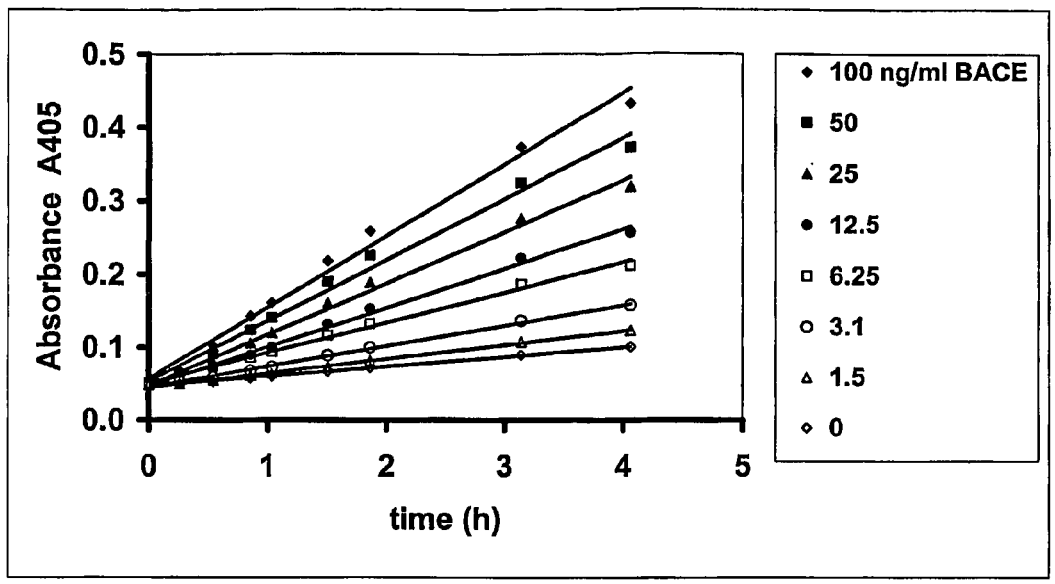
Figure 12B:
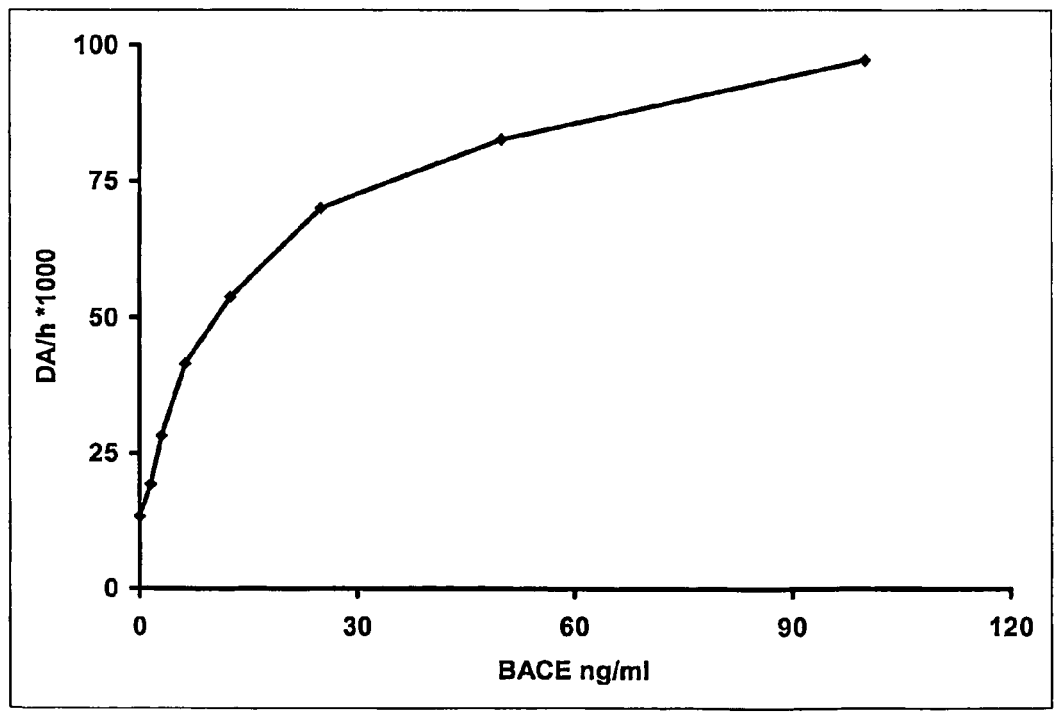

FIG. 10. Time and concentration dependence of aggrecanase assay using modified pro-caspase-3 with an aggrecanase recognition sequence as target. FIG. 10A shows the increase of absorbance with time for the indicated concentrations of aggrecanase (in ng/ml). FIG. 10B shows the rate of absorbance increase as a function of agqrecanase concentration. The inset is an expanded view of the low concentration range;

FIG. 11. Time arid concentration dependence of TACE activity assay using modified pro-caspase-3 with a TACE recognition sequence as target FIG. 11A shows the increase of absorbance with time for the indicated concentrations of TACE. FIG. 11B shows the rate of absorbance increase as a function of TACE concentration. FIG. 12. Time and concentration dependence of BACE assay using modified pro-caspase-3 as target. FIG. 12A shows the increase of absorbance with time for the indicated concentrations of BACE. FIG. 12B shows the rate of absorbance increase as a function of BACE concentration.

Figure 13A:
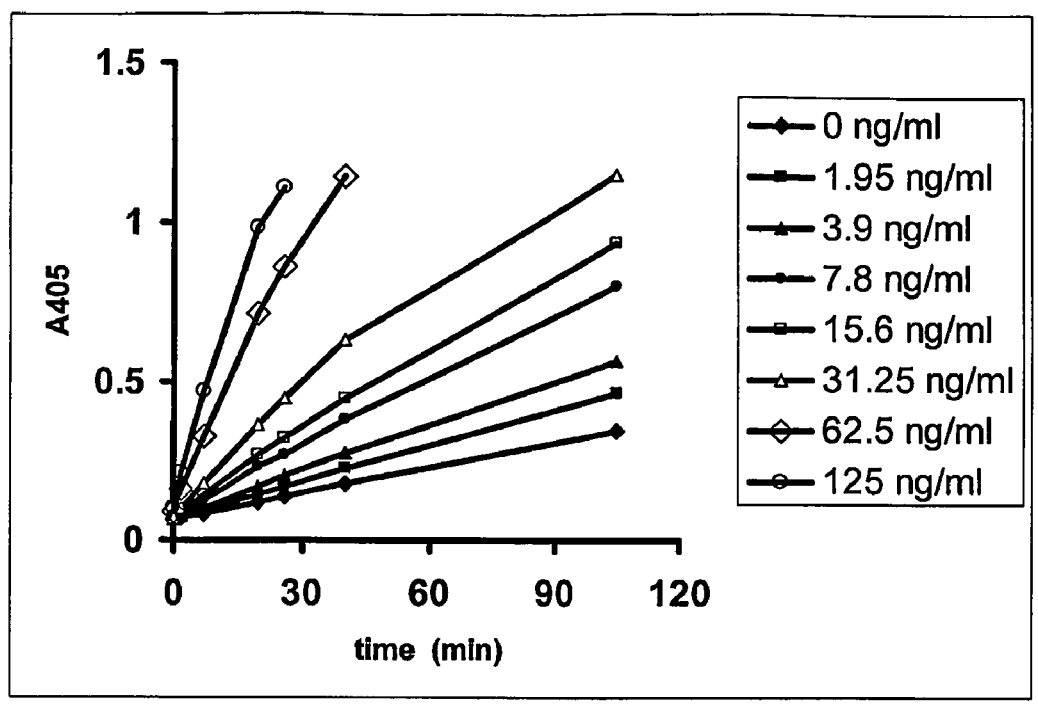
Figure 13B:
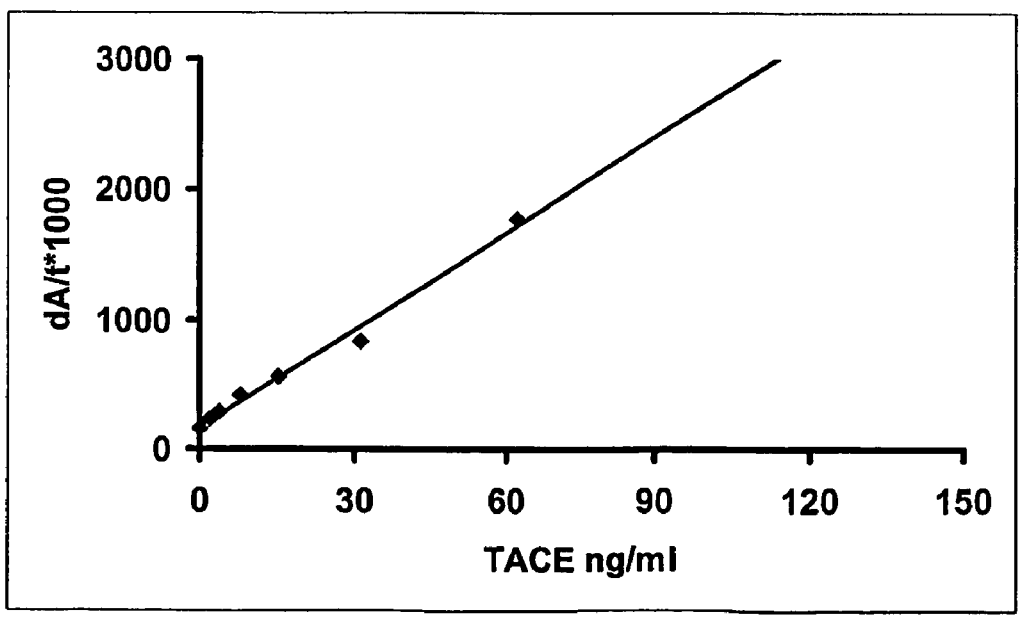

FIG. 13. Time and concentration dependence of TACE activity assay using modified pro caspase-3 with a TACE recognition sequence as target after capturing TACE to a specific monoclonal antibody coated to a microtiterplate. FIG. 13A shows the increase of absorbance with time for the indicated concentrations of TACE. FIG. 13B Shows the rate of absorbance increase as a function of TACE concentration.

The invention can be used to determine catalytically active proteases involved in biotechnologically or (patho) physiologically interesting processes. "Determining a protease" means both qualitative analysis, i.e. detecting the presence of the protease, particularly its activity, and quantitative analysis, i.e. quantifying the protease activity present in a sample.

Examples of interesting proteases are given in Table II. This table includes proteases with established clinical or biotechnological relevance, as well as proteases which could be involved in relevant (patho) physiological processes based on current knowledge. The invention discloses methods suitable to assay members of all four known protease families, serine proteases, cysteine proteases, metalloproteases and aspartyl proteases. In contrast to existing technology the invention discloses methods to assay proteases with any target recognition sequence. In many cases proteases do not occur in biological fluids in the catalytically active form but in an inactive zymogen or pro-enzyme form. In such cases conversion to the active form is required before measurement. Depending on the zymogen, conversion to the active protease can be accomplished by limited proteolytic digestion, treatment with certain chemicals or mild denaturation by application of heat or e.g. sodium dodecylsulphate. Methods based on the invention can be very sensitive and specific and can easily be adapted for automation using generally available laboratory equipment. The invention appears to be most applicable in biotechnology, animal or human health research laboratories and hospitals and clinical laboratories and pharmaceutical research laboratories. Other applications might be in quality control in pharmaceutical or food-processing industries.

The invention uses a pro-enzyme as target substrate for the protease which needs to be assayed which can be converted to an active enzyme by one or more specific proteolytic events and subsequently the activity of the active enzyme is detected using standard technology known in the art (FIG. 2). More particularly the invention relates to the choice of the pro-enzyme. Although many pro-enzymes can be chosen as a basis for modification and development of an assay for a particular protease, most pro-enzymes have certain limitations in the sequence that can be modified and consequently the proteases that can be measured. In the present invention we describe an improved method based on a particular group of pro-enzymes which does not have these limitations, thus enabling assay development for virtually any protease irrespective of its substrate preferences.

Current methodology is mostly based on pro-enzymes belonging to the serine protease family although certainly not limited to this family. The activation recognition sites of most known proteases of the serine protease family show certain similarities. Although the sequence at the N-terminal side of the activation site is very variable, the sequence at the C-terminal side of the activation site has a great degree of similarity in a large number of pro-enzymes belonging to the serine protease family (Table III). It appears that charged amino acid residues are not tolerated at the positions P1 or P2'. Furthermore a very strong preference for aliphatic amino acid side chains appears to occur since almost exclusively Ile, Val, Leu or Ala residues occur in these positions in a large number of serine proteases. Also at the positions P3' and P4' there appear to exist severe restrictions in sequence variety with a very strong preference for small uncharged amino acid residues like Gly. The restrictions in sequence appear to be intimately coupled to the mechanism of activation of this family of pro-enzymes.

The present invention discloses that modified pro-caspases are ideal candidates for use as target substrates for proteases. Pro-caspases are a family of cysteine protease pro-enzymes which are involved in apoptosis, regulated cell death (FIG. 5). The caspases form a cascade in which one active caspase can activate an (other) pro-caspase leading to a chain of reactions in the cell resulting in cell death. Furthermore many of the caspases show autocatalytic activation of their pro-enzyme form. Caspases are very specific proteases. They recognize sequences with several negatively charged amino acid residues like Glu or Asp and cleave C-terminal of such sequences. Typical recognition sequences within the caspase family are summarized in table IV. Each member of the caspase family has a certain preference for a certain sequence although there is considerable overlap with the substrate sequence of other caspases. The activation sequence of many if not all pro-caspases is a sequence that itself can be cleaved by one or more active caspases. Due to their involvement in apoptosis, a process likely involved in many diseases such as e.g. cancer, a large number of peptide substrates cleavable by caspases and resulting in the liberation of a coloured or fluorescent group have been developed and are commercially available (table V).

In the present invention it is disclosed that introduction of a novel not naturally occurring target cleavage site for a protease that needs to be assayed in the normal activation area of a pro-caspase leads to a modified pro-caspase that can be cleaved and activated by the protease of choice. Thus such modified pro-caspases are ideally suited for use as detection enzymes to develop assays for a variety of proteases. It is also shown that the novel not naturally occurring cleavage site can be chosen to vary considerably in length and actual amino acid sequence without the limitations as were found for serine proteases in the state of the art. It is, however, submitted that care should be taken that the modified pro-caspase still is able to be activated into an active caspase which is able to exert its normal proteolytic activity. Determination whether the modifications leave the function of the caspase intact are well within the skill of the person of skill in the art.

The present invention also discloses modified pro-caspases which can be used to detect proteases hitherto not detectable with current methodology or with great difficulty or low efficiency. Preferably the modification of the pro-caspase is such that the normal activation reaction by e.g. other caspase family members or auto-activation is prevented. This can be accomplished by alteration or even complete removal of the normal activation sequence. The novel target activation sequence, recognizable and cleavable by the protease of choice, can replace the normal activation sequence but can also be introduced elsewhere in the pro-caspase sequence. The site for insertion of a target sequence is not critical, although care should be taken that cleavage of the modified pro-caspase still results in formation of an active caspase. Again, checking if such activity is retained and adapting the insertion site, is well within the realm of the skilled person.

Apart from modifications around the activation site, other secondary modifications could be included, directed at improving the properties of the pro-caspase or caspase formed after activation for the particular application. Useful secondary modifications include: modifications increasing the (thermal) stability of the pro-caspase or activated caspase, conferring resistance to other, non-target, proteases, conferring resistance to naturally occurring or synthetic inhibitors, conferring reactivity to certain antibodies or ligands, aiding expression and/or purification or alterations increasing activity of the activated form or decreasing activity of the pro-form. In general, but not always, such secondary mutations will be in another part of the caspase and not near the activation site. It is also possible to introduce more than one novel activation site, thus resulting in a target substrate that can be used for a variety of proteases with different substrate specificity.

Many members of the caspase family are potentially suitable for modification to be used as target for a protease. Particularly caspase-3 and caspase-7 are very suitable since these two caspases are very stable and easy to produce by existing methodology. Also it appears that activation of pro-caspase-3 and -7 is critically dependent on proteolytic cleavage in the activation region. Furthermore very efficient substrates for these caspases exist (table V). For detection of the caspase activity, these substrates should have amino acid sequences that are recognised and cleaved by the caspase which is used in the test (table V shows a number of known sequences and the recognising caspases). Most preferably used is the amino acid sequence DEVD (asp-glu-val-asp) (SEQ ID NO: 37). Further, the cleaved substrate should yield a signal for detection. This can, for instance, be achieved by linking para-nitro-anilide, 7-amino-4-trifluoro methyl coumarine, amino methyl coumarine or any other color, fluorescence or luminescence generating compound directly to the C-terminus of the peptide sequence which is recognised by the caspase. Then these compounds will become free in the test solution as a result of caspase action and the presence of these compounds can quantitatively be detected e.g. by spectrophotometry, fluorimetry or luminometry. Other embodiments which yield a qualitative or quantitative signal after cleavage by the caspase are known in the art and can be easily comprised in the assay of the invention by a person skilled in the art. Such embodiments could, for example, employ antibodies specifically recognizing the active form of caspase and cellular assays of detecting caspase action.

To introduce a new amino acid sequence conferring a new desired target specificity for a protease into an existing pro-caspase several methodologies known to a person skilled in the art can be followed. In particular recombinant DNA technology appears to be an attractive option. A cDNA sequence coding for a particular pro-caspase must be available. Such sequences are known and can be obtained from publicly available databases. Such a cDNA can be obtained with existing technology such as from mRNA isolated from a suitable cell line or tissue by reverse transcriptase polymerase chain reaction using primers devised with the aid of the known sequence. Many alternative procedures are known in the art to obtain a specific cDNA sequence. The coding sequence can be adapted to improve later expression into protein and to facilitate later introduction of changes aimed at altering the activation specificity of the resulting pro-caspase after expression. Also a suitable promoter and other regulatory sequences have to be added as is known in the art. The coding sequence or altered coding sequence is introduced into a vector such as a plasmid or virus to enable introduction into a cell system for expression. Expression can in general be performed in eukaryotic animal cell or yeast expression systems or in prokaryotic bacterial expression systems. These systems are known in the art and are in many cases available in commercial form. After the expression step procedures to free the expressed protein from the cells or isolate it from the culture medium are generally required. Very likely further purification of the expressed protein will be required. Many procedures for these steps are known in the art.

When an expression plasmid is constructed containing the natural unmodified coding sequence of a pro-caspase, appropriate modifications can be added by any of the known methods of site directed mutagenesis or newer methods involving polymerase chain reaction. To ease construction of a large number of different coding sequences differing in the sequences coding for the novel activation site in the expressed protein it might be convenient to introduce some extra alterations in the coding sequence leading to new restriction sites that can be used to introduce many different modifications in the activation site in an easy and quick way by introduction of synthetic oligonucleotides between these restriction sites. These extra alterations can either be so called silent mutations, not altering the amino acid sequence, or changes which alter the protein sequence but have no adverse effects on the protein function. A further advantage of this approach employing newly introduced restriction sites and subsequent oligo insertion, is the lower chance on secondary unwanted mutations that might arise during polymerase chain reaction based methods. In the same way further modifications to improve the properties of the pro-caspase could be introduced. Such a modified pro-caspase can be part of an assay kit containing all necessary materials to perform one or a number of determinations. Typically, such a kit comprises containers with sufficient quantities of modified pro-caspase, a suitable substrate to detect caspase activity, a suitable standard preparation to quantify the protease to be measured and materials to prepare buffer solutions. Furthermore, a kit might also contain specific antibodies recognizing the protease to be assayed to increase the specificity of the assay by specific quenching of the activity of a specific protease, interfering protease or specific binding of a protease. A kit might also contain one or more assay plates in e.g. the regular 96-well, 384-well or 1536-well format. It might be advantageous to add stabilizers to the modified pro-caspase to increase its stability during transport and storage. Such stabilizers could be other proteins like albumin or gelatin, carbohydrates like mannitol, anti oxidants, detergents or other organic chemicals. Furthermore inorganic salts might also have beneficial effects on stability. Most conveniently the modified pro-caspase is present in lyophylized form and has to be reconstituted by adding buffer or water shortly before use. In addition, a description how to perform the determination, preparing the samples and calculate the activity is included. Another possibility to increase the specificity as known in the art is to employ an immunocapture procedure: first the protease to be measured is caught using a specific immobilized (mono- or polyclonal) antibody followed by measurement of the activity of the caught protease. Alternatively a kit or device might be of the "dipstick" type where all necessary reagents present in a dry form are immobilized on a strip or dot of material. The following examples are just illustrations of the invention and by no means limit the applicability or scope of the invention.

EXAMPLES

Example 1

Limitation of Pro-Enzymes of Serine Proteases as Detection Enzyme

In this example the limitations of using pro-enzymes of the serine protease family as detection enzyme are shown. Pro-enzymes of the serine protease family such as pro-urokinase have a number of suitable properties for their use as detection enzymes to measure the activity of proteases: The active form of the serine proteaes is easily measured with chromogenic or fluorogenic peptide substrates; the difference in activity between pro-enzyme and active enzyme is generally high; the enzymes are generally stable and can be very specific. A major drawback of using serine-protease family members as detection enzyme are the sequence limitations in the C-terminal part of the activation sequence. The newly formed N-terminus that results from cleavage of the activation sequence plays an essential role in generation of the active enzyme. Comparison of these sequences from a number of serine-proteases family members (table II) reveals a strong homology in this region suggesting an involvement in the function. The flexibility in sequence in this region was in more detail investigated for pro-urokinase. The complete cDNA coding for human pro-urokinase was cloned into an expression vector enabling expression of the protein in eukaryotic cells (EP 691 409). With polymerase chain reaction using primers 5'-ACC ATC GAt AAC CAG CCC TGG-3' (SEQ ID NO: 5) and 5'-CCG CCT cga gGT CTT TTG GCC-3'(SEQ ID NO: 6) (mutations indicated as lowercase letters) two new unique restriction sites ClaI and XhoI were introduced flanking the region coding for the activation site. The resulting plasmid vector was used to construct a variety of pro-urokinase coding sequences, coding for pro-urokinase molecules with different activation sites by cutting the plasmid with ClaI and XhoI and insertion and ligation of two partially complementary oligonucleotides coding f or the required mutated aminoacid sequence. The oligonucleotide pairs used for construction of the various expression plasmids are summarised in Table VI. The newly constructed plasmids were transfected into CHO cells and medium from the transiently transfected cells was collected. Concentrations of pro-urokinase variants in the conditioned media were determined by an ELISA recognising the protease domain of the molecule, thus ensuring a similar response for all variants. Pro-urokinase variants were immuno-captured to a plate coated with antibody recognizing both pro-urokinase and active urokinase and not inhibiting the activity of the latter or interfering with the conversion of the pro-enzyme form to the active form. Subsequently pro-urokinase variants were activated with plasmin and after washing of the plate, the resulting urokinase activity was determined by addition of buffer and pyro-Glu-Gly-Arg-pNA (S2444, a commercially available urokinase substrate). The results summarized in FIG. 6 show that an Ile, Leu or Val residue in the P1' position is essential. At the P2' position also a strong preference for aliphatic residues exists, but other residues are tolerated, albeit leading to a strongly reduced activity. The presence of Gly at P3' and P4' appears critical. From these results it can be concluded that the possibility for variation in the P1'-P4' sequence is very limited, resulting in the impossibility to use pro-urokinase and other members of the serine protease family as detection enzymes for those proteases having a recognition sequence not compatible with the above mentioned restraints in the P1'-P4' region using the direct activation method.

Example 2

Preparation of Modified Pro-Caspase 3 with Aggrecanase or TACE Specific Cleavage Site A cDNA coding for caspase-3 cloned into an expression vector having a sequence coding for a His-tag enabling rapid purification using Ni chelate chromatography and regulatory sequences enabling expression in *E. coli* was obtained from the ATCC. This plasmid was used as a basis for construction of similar plasmids coding for a variety of caspase-3 variants with modifications in their activation sequence. To enable rapid construction of variants two new silent restriction sites were introduced by PCR (FIG. 7a). After digestion with BamHI and EcoRI a novel coding sequence can be introduced using two oligonucleotides. To test the capability of Caspase-3 as detection enzyme two different sequences coding for an activation sequence for aggrecanase (AD-AMTS-4) and TNFα converting enzyme (TACE\ADAM 17) respectively were introduced, using appropriate oligonucleotides (FIG. 7b and Table VII). Both aggrecanase and TACE could not or with very low efficiency be measured using a pro-urokinase derived substrate. The resulting plasmids were used to transform *E. coli* (strain B121 (DE3) pLys). Cultures were grown to an OD 0.45-0.7, cooled to 30° C. and induced with 1 mM IPTG. After 45 min shaking at 30° C. cells were centrifuged (10 min 6000 rpm (ca. 5000×g) at 4° C.) and either directly used or stored frozen at −20° C. Bacterial pellets were mixed with lysis buffer (50 mM Tris.HCl pH 8.0, 300 mM NaCl, 10 mM imidazol) and Bugbuster™ (Novagen) incubated at 4° C. while stirring for 30 min and centrifuged at 6000 rpm (ca. 5000×g) for 10 min at 4° C.

The supernatant was brought on a nickel Sepharose (Amersham Biosciences) column (2 ml column volume for 30-50 ml of original culture volume) and subsequently washed with 20 column volumes of 50 mM Tris HCl pH 8.0, 300 mM NaCl, 20 mM imidazol, (wash buffer) and eluted with elution buffer (50 mM Tris HCl pH 8.0, 300 mM NaCl, 250 mM imidazol). The peak fractions were desalted using a PD-10 column (Amersham Biosciences) equilibrated with 10 mM Tris HCl pH 7.0, 1.5 mM NaCl, 0.01% (v/v) BRIJ 35 buffer (FIG. 8).

Example 3

Preparation of Modified Pro-Caspase 7

Analogously as described for pro-caspase-3 in Example 2 cDNA and expression vectors coding for variants of pro-caspase-7 were constructed containing sequences coding for pro-caspase-7 variants with activation sequences for TACE and aggrecanase. The oligonucleotides to introduce the novel activation sequences were exactly the same as used for pro-caspase-3 variants (see Table VII).

Transformation, expression and purification of pro-caspase-7 variants was performed as described for pro-caspase-3 variants in example 2.

Example 4

Characterization of Modified Procaspases

Gel-electrophoresis showed that all caspase variants were predominantly in the single chain 32 kD forms (FIG. 9).

Caspase activity was measured as follows: 10 µl (1-100 ng) of purified modified caspase-3 or -7 with an aggrecanase or TACE specific cleavage site (see example 2 and Table VII) was mixed with 60 µl of assay buffer (50 mM Tris HCl pH 7.6, 1.5 mM NaCl, 0.5 mM CaCl2, 1 µM ZnCl2, 0.01% (v/v) BRIJ 35) and 10 µl of purified aggrecanase (ADAMTS-4) or TACE (ADAM-17).

After overnight incubation at room temperature 10 µl of 100 mM DTT and 10 µl of 8 mM DEVD-pNA (BioSource) was added and A405 was measured after 0-6 h of incubation at 37° C. in a moist chamber. Assays were performed in 96-well flat bottomed polystyrene microtiter plates and absorbance measurements were performed with at Titertek Multiskan™ plate reader. A low background activity in the pro-caspase-3 and -7 variants most likely caused by the presence of small amounts of contaminating active forms was detected. Upon incubation of the various pro-caspase variants with their respective target enzymes a clear increase in caspase activity was observed.

Example 5

Determination of Aggrecanase Activity Using Modified Pro-Caspases

Protocol for detection of aggrecanase activity using pro-caspase-3 or -7 variants with an aggrecanase cleavable activation sequence (see Example 2 and Table VII). The detection is performed in two steps, in the first step the pro-caspase variant is incubated with its target enzyme and in the second step the amount of pro-caspase variant converted to active caspase variant is detected by incubation with a caspase substrate.

Wells of a 96-well microtiter plate were filled with 10 µl (1-100 ng) of pro-caspase-3 or -7 variant and 60 µl assay buffer (50 mM Tris HCl, 1.5 mM NaCl, 0.5 mM CaCl2, 1 µM ZnCl$_2$ 0.01% (v/v) BRIJ35).

10 µl aggrecanase diluted in assay buffer as indicated was added. After incubation at 37° C. overnight 10 µl of 100 mM DTT and 10 µl of 8 mM DEVD-pNA (BioSource) in H$_2$O were added. The plate was incubated at 37° C. in a moist chamber for 0-6 h, and A405 was measured after regular intervals using a Titertek Multiskan plate reader. For each enzyme concentration the absorbance change was plot against incubation time (FIG. 10a). The slopes of these curves were plot against aggrecanase concentration (FIG. 10b).

Example 6

Determination of TNF Alpha Converting Enzyme Activity Using Modified Pro-Caspases Similarly as described for aggrecanase (example 5) the appropriate pro-caspase-3 and -7 variants were incubated with purified TACE using a protocol similar to that described in example 5. The results are shown in FIG. 11a, b.

Example 7

Determination of β Amyloid Converting Enzyme (BACE-1) Using Modified Pro-Caspases Similarly as described for aggrecanase and TACE a pro-caspase-3 variant was produced containing a sequence cleavable by β-amyloid converting enzyme (BACE-1) (see Table VII and FIG. 7 a,b).

10 µl of purified modified caspase-3 with a BACE-1 specific cleavage was mixed with 300 µl 10 mM Na-acetate pH 5.1, 1.5 mM NaCl, 0.01% (v/v) BRIJ35 and 10 µl BACE-1 enzyme. After overnight activation at room temperature 10 µl of 100 mM DTT, 10 µl of 8 mM DEVD-pNA (BioSource) and 30 µl of 100 mM Tris HCl pH 8.0, 1.5 mM NaCl, 0.01% (v/v) BRIJ 35 was added and A405 was measured at regular intervals after 0-6 h of incubation at 37° C. in a moist chamber. Assays were performed in 96-well flat bottomed polystyrene microtiter plates and absorbance measurements were performed with a Titertek Multiskan™ plate reader.

The results for the detection of BACE-1 activity were shown in FIG. 12a, b.

Example 8

Immuno-Capture Assay for TACE

For some proteases or applications it is of use to have an immuno-capture format. In such a format the protease to be detected, generally present in a biological sample at low concentration in the presence of a variety of disturbing compounds such as salts, other proteases, protease inhibitors etc., is specifically removed from the biological sample using e.g. a microtiter plate coated with an antibody specifically recognizing and binding the target protease. After binding of the target protease to the plate the sample containing the interfering substances is removed and the plate can be washed if required and a clearly defined solution with purified components can be added. Such an approach has several advantages and is frequently used for the detection of closely related proteases with overlapping substrate specificity such as the MMP family of proteases.

A microtiter plate (Costar EIA/RIA 8 well flat bottom) is coated with 100 µl per well of 10 µg/ml goat-anti-mouse IgG and 2 µl/ml mouse monoclonal antibody recognizing TACE overnight at 4° C. in Na-carbonate buffer pH 9.6. After washing 4 times with 0.01 M Na-phosphate pH 7.0, 0.15 M NaCl, 0.05% (v/v), the plate is used as an immuno-capture plate. Samples containing TACE are pipetted into the plate and incubated at 4° C. overnight. After capture the plate is emptied and washed, and subsequently filled with 10 µl (1-100 ng) of pro-caspase-3 variant with TACE cleavage site (see Table VII) and 60 µl assay buffer and incubated at 37° C. for 2 h. Thereafter DEVD-pNA is added and again incubated at 37° C., the absorbance is measured after 0-6 h incubation. A plot of the absorbance versus incubation time and absorbance versus TACE concentration is shown in FIG. 13 A, B.

TABLE I

| | Classes of proteases | | | |
|---|---|---|---|---|
| Name | EC number | Active site residues | | |
| Serine proteases | 3.4.21 | Ser | His | Asp* |
| Cysteine proteases | 3.4.22 | Cys | His | Asp* |
| Aspartic proteases | 3.4.23 | Asp | Asp | |
| Metallo proteases | 3.4.24 | His | His | Me$^{2+}$** |

*Asp not always present
**His residues involved in chelating metal ion.
Metal ion is often Zn$^{2+}$

TABLE II

Some clinically important proteases

| Protease | Involved in | Diseases |
|---|---|---|
| Factor VIIa | Blood clotting | Bleeding/thrombolysis |
| Factor IXa | Blood clotting | Bleeding/thrombolysis |
| Factor Xa | Blood clotting | Bleeding/thrombolysis |
| APC | Blood clotting | Bleeding/thrombolysis |
| Thrombin | Blood clotting | Bleeding/thrombolysis |
| t-PA | Fibrinolysis/peri-cellular proteolysis | |
| u-PA | Fibrinolysis/peri-cellular proteolysis | Bone degradation |
| plasmin | Fibrinolysis/peri-cellular proteolysis | Lung emphysema |
| trypsin | Digestion | Pancreatitis |
| chymotrypsin | Digestion | Pancreatitis |
| enterokinase | Digestion ( ) | Pancreatitis |
| pepsin | Digestion | Pancreatitis |
| Cathepsin B, H, D | Lysosomal digestion | |
| Cathepsin K | Lysosomal digestion | Bone degradation |
| Cathepsin G | Lysosomal digestion | Lung emphysema |
| Cathepsin L | Lysosomal digestion | |
| Cathepsin V | Lysosomal digestion | |
| Cathepsin S | Lysosomal digestion | |
| Renin | Blood pressure regulation | High bloodpressure |
| ACE | Blood pressure regulation | High bloodpressure |
| MMPs | Invasion, tissue remodeling | Cancer, arthritis inflammation |
| Elastase | Elastin degradation | Lung emphysema |
| C1r | Complement activation | Inflammation |
| C1s | Complement activation | Inflammation |
| HIV protease | Virus assembly | AIDS |
| Caspases | Apoptosis | Cancer |

TABLE III

Examples of pro-enzymes of the serine protease family

| Proenzyme | Bond split upon activation $P_4$-$P_3$-$P_2$-$P_1$ ↑ $P'_1$-$P'_2$-$P'_3$-$P'_4$ | Sequence Identification No. |
|---|---|---|
| Prothrombin | Glu-Gly-Arg ↑ Ile-Val-Glu-Gly | (SEQ ID NO: 7) |
| Pro-urokinase | Arg-Phe-Lys ↑ Ile-Ile-Gly-Gly | (SEQ ID NO: 8) |
| Trypsinogen | Asp-Asp-Lys ↑ Ile-Val-Gly-Gly | (SEQ ID NO: 9) |
| Chymotrypsinogen | Leu-Ser-Arg Ile-Val-Asn-Gly | (SEQ ID NO: 10) |
| Pro-elastase | Val-Tyr-Arg ↑ Val-Val-Gly-Glu | (SEQ ID NO: 11) |
| Pro-subtilisin | Ala-Gly-Lys ↑ Ser-Asn-Gly-Glu | (SEQ ID NO: 12) |
| Coagulation factor V | Gly-Ile-Arg ↑ Ser-Phe-Arg-Phe | (SEQ ID NO: 13) |
| Coagulation factor VII | Pro-Gln-Arg ↑ Ile-Val-Gly-Gly | (SEQ ID NO: 14) |
| Coagulation factor IX | Asp-Phe-Thr-Arg ↑ Val-Val-Gly-Gly | (SEQ ID NO: 15) |
| Coagulation factor X | Asn-Leu-Thr-Arg ↑ Ile-Val-Gly-Gly | (SEQ ID NO: 16) |
| Coagulation factor XII | Ser-Met-Thr-Arg ↑ Val-Val-Gly-Gly | (SEQ ID NO: 17) |
| Coagulation factor XI | Ile-Lys-Pro-Arg ↑ Ile-Val-Gly-Gly | (SEQ ID NO: 18) |
| Kallikrein | Thr-Ser-Thr-Arg ↑ Ile-Val-Gly-Gly | (SEQ ID NO: 19) |
| Plasminogen | Pro-Gly-Arg ↑ Val-Val-Gly-Gly | (SEQ ID NO: 20) |
| Cathepsin G | Ala-Gly-Glu ↑ Ile-Ile-Gly-Gly | (SEQ ID NO: 21) |

Sequences obtained from SWISS-PROT, GenBank or PIR databases.

TABLE IV

Some substrate cleavage sites for various caspases
Preferred sequences

| Caspase-1 | |
|---|---|
| YEVD ↑ | (SEQ ID NO: 22) |
| WEHD ↑ | (SEQ ID NO: 23) |
| LEVD ↑ | (SEQ ID NO: 24) |
| WVAD ↑ | (SEQ ID NO: 25) |
| Caspase-2 | |
| VDVAD ↑ | (SEQ ID NO: 26) |
| DEHD ↑ | (SEQ ID NO: 27) |
| LDESD ↑ | (SEQ ID NO: 28) |
| Caspase-3 | |
| IETD ↑ | (SEQ ID NO: 29) |
| DMQC ↑ | (SEQ ID NO: 30) |
| Caspase-4 | |
| LEVD ↑ | (SEQ ID NO: 24) |
| WEHD ↑ | (SEQ ID NO: 23) |
| LEHD ↑ | (SEQ ID NO: 31) |
| WVAD ↑ | (SEQ ID NO: 25) |
| Caspase-5 | |
| WEHD ↑ | (SEQ ID NO: 23) |
| LEHD ↑ | (SEQ ID NO: 31) |
| LEAD ↑ | (SEQ ID NO: 32) |
| Caspase-6 | |
| VEID ↑ | (SEQ ID NO: 33) |
| VEHD ↑ | (SEQ ID NO: 34) |
| VKMD ↑ | (SEQ ID NO: 35) |
| VNLD ↑ | (SEQ ID NO: 36) |
| Caspase-7 | |
| DEVD ↑ | (SEQ ID NO: 37) |
| Caspase-8 | |
| IETD ↑ | (SEQ ID NO: 29) |
| LETD ↑ | (SEQ ID NO: 38) |

TABLE IV-continued

Some substrate cleavage sites for various caspases
Preferred sequences

Caspase-9

| LEHD ↑ | (SEQ ID NO: 31) |
| VEHD ↑ | (SEQ ID NO: 34) |

Caspase-10

| IEAD ↑ | (SEQ ID NO: 39) |
| AEVD ↑ | (SEQ ID NO: 40) |
| VEHD ↑ | (SEQ ID NO: 34) |

TABLE V

Peptide substrates for detection of caspase activity

| Substrate | Sequence Identification No. | Preferred caspase |
|---|---|---|
| VAD-X | — | 1 |
| DEVD-X | (SEQ ID NO: 37) | 3, 6, 7, 8 |
| VEID-X | (SEQ ID NO: 33) | 6, 8 |
| IETD-X | (SEQ ID NO: 29) | 8, 9, 10 |
| WEHD-X | (SEQ ID NO: 23) | 1, 4, 5 |
| YVAD-X | (SEQ ID NO: 98) | 1, 4, 5 |
| VDVAD-X | (SEQ ID NO: 26) | 2 |

X can be -pNA (para-nitro-anilide), -AFC (7-amino-4 trifluoro methyl coumarine), -AMC (amino methyl coumarine), or any other chromogenic or fluorogenic leaving group.

TABLE VI

Oligonucleotides used for construction of pro-urokinase variants

```
                                                                         Sequence
                                                                         Identification No.
PRFKIGGG  Sense        S    R    P    R    F    K    I    G    G    G    E    F    T    T    (SEQ ID NO: 42)
                 5'-TCG AGG CCC CGC TTT AAG ATT GGG GGA GAA TTC ACC ACC AT-3'                  (SEQ ID NO: 41)
          A-sense 5'-C GAT GGT GGT GAA TTC TCC CCC GCC AAT CTT AAA GCG GGG CC-3'               (SEQ ID NO: 43)
PRFKIAGG  Sense        S    R    P    R    F    K    I    A    G    G    E    F    T    T     (SEQ ID NO: 45)
                 5'-TCG AGG CCC CGC TTT AAG ATT GCC GGG GGA GAA TTC ACC ACC AT-3'              (SEQ ID NO: 44)
          A-sense 5'-C GAT GGT GGT GAA TTC TCC CCC GGC AAT CTT AAA GCG GGG CC-3'               (SEQ ID NO: 46)
PRFKIEGG  Sense        S    R    P    R    F    K    I    E    G    G    E    F    T    T     (SEQ ID NO: 48)
                 5'-TCG AGG CCC CGC TTT AAG ATT GAA GGG GGA GAA TTC ACC ACC AT-3'              (SEQ ID NO: 47)
          A-sense 5'-C GAT GGT GGT GAA TTC TCC CCC TTC AAT CTT AAA GCG GGG CC-3'               (SEQ ID NO: 49)
PRFKAIGG  Sense        S    R    P    R    F    K    A    I    G    G    E    F    T    T     (SEQ ID NO: 51)
                 5'-TCG AGG CCC CGC TTT AAG GCC ATT GGG GGA GAA TTC ACC ACC AT-3'              (SEQ ID NO: 50)
          A-sense 5'-C GAT GGT GGT GAA TTC TCC CCC AAT GGC CTT AAA GCG GGG CC-3'               (SEQ ID NO: 52)
PRFKILGG  Sense        S    R    P    R    F    K    I    L    G    G    E    F    T    T     (SEQ ID NO: 54)
                 5'-TCG AGG CCC CGC TTT AAG ATT CTT GGG GGA GAA TTC ACC ACC AT-3'              (SEQ ID NO: 53)
          A-sense 5'-C GAT GGT GGT GAA TTC TCC CCC AAG AAT CTT AAA GCG GGG CC-3'               (SEQ ID NO: 55)
PRFKLIGG  Sense        S    R    P    R    F    K    L    I    G    G    E    F    T    T     (SEQ ID NO: 57)
                 5'-TCG AGG CCC CGC TTT AAG CTT ATT GGG GGA GAA TTC ACC ACC AT-3'              (SEQ ID NO: 56)
          A-sense 5'-C GAT GGT GGT GAA TTC TCC CCC AAT AAG CTT AAA GCG GGG CC-3'               (SEQ ID NO: 58)
PRFKIVGG  Sense        S    R    P    R    F    K    I    V    G    G    E    F    T    T     (SEQ ID NO: 60)
                 5'-TCG AGG CCC CGC TTT AAG ATT GTG GGG GGA GAA TTC ACC ACC AT-3'              (SEQ ID NO: 59)
          A-sense 5'-C GAT GGT GGT GAA TTC TCC CCC CAC AAT CTT AAA GCG GGG CC-3'               (SEQ ID NO: 61)
PRFKVIGG  Sense        S    R    P    R    F    K    V    I    G    G    E    F    T    T     (SEQ ID NO: 63)
                 5'-TCG AGG CCC CGC TTT AAG GTG ATT GGG GGA GAA TTC ACC ACC AT-3'              (SEQ ID NO: 62)
          A-sense 5'-C GAT GGT GGT GAA TTC TCC CCC AAT CAC CTT AAA GCG GGG CC-3'               (SEQ ID NO: 64)
PRFKDIGG  Sense        S    R    P    R    F    K    D    I    G    G    E    F    T    T     (SEQ ID NO: 66)
                 5'-TCG AGG CCC CGC TTT AAG GAT ATT GGG GGA GAA TTC ACC ACC AT-3'              (SEQ ID NO: 65)
          A-sense 5'-C GAT GGT GGT GAA TTC TCC CCC ATT ATC CTT AAA GCG GGG CC-3'               (SEQ ID NO: 67)
```

TABLE VII

Oligonucleotide cassettes used for Construction of modified-caspase expression vectors Aggrecanase (ADAMTS4)

```
              D    M    E    L    P    L    P    R    N    I    T    E    G    E  ^  A    R
5'- GA TCC GAC ATG GAG CTC CCA CTG CCT CGA AAC ATC ACT GAG GGT GAA GCC CGA
3'-        G CTG TAC CTC GAG GGT GAC GGA GCT TTG TAG TGA CTC CCA CTT CGG GCT
    G    S    V    I    L    T    V    K    P    I    F    E
                                                                                             (SEQ ID NO: 69)
GGC AGC GTG ATC CTT ACC GTA AAG CCC ATC TTC GAG G -3'                                        (SEQ ID NO: 68)
CCG TCG CAC TAG GAA TGG CAT TTC GGG TAG AAG CTC CTT AA-5'                                    (SEQ ID NO: 70)
```

TACE (TNFα converting enzyme)

```
              P    L    A    Q    A  ^  V    R    S    S    S    R
                                                                                             (SEQ ID NO: 72)
5'-GA TCC CCA TTG GCA CAG GCA GTT AGA TCT TCA TCA CGG G    -3'                               (SEQ ID NO: 71)
3'-       G GGT AAC GCT GTC CGT CAA TCT AGA AGT AGT GCC CTT AA-5'                            (SEQ ID NO: 73)
```

TABLE VII-continued

Oligonucleotide cassettes used for Construction of modified-caspase expression vectors BACE (β-amyloid converting enzyme)

```
                                                                        (SEQ ID NO: 75)
          K   T   E   E   I   S   E   V   N   L ^ D   A   E   F   R   H   D   S
                                                                        (SEQ ID NO: 74)
5'-GA TCC AAA ACA GAA GAG ATC TCC GAA GTT AAC CTG GAC GCA GAG TTT CGT CAT GAC TCA G      -3'
                                                                        (SEQ ID NO: 76)
3'-    G TTT TGT CTT CTC TAG AGG CTT CAA TTG GAC CTG CGT CTC AAA GCA GTA CTG AGT CTT AA-5'
```

The indicated oligonucleotide pairs were ligated into BamHI and EcoRI cut pro-caspase-3 or pro-caspase-7 expression vector to obtain expression vectors coding for pro-caspase variants with cleavage/activation sites for ADAMTS4, TACE and BACE. Recognition sequences of the proteins are indicated in bold above the oligonucleotides, cleavage sites are indicated with an ô. See also FIG. 7.

The invention claimed is:

1. A method of detecting the presence and/or activity of a protease with a desired target specificity, or of its precursor after activation, comprising incubating a sample comprising said protease with a target of said protease, determining proteolytic cleavage of said target, and correlating data obtained therefrom in order to determine the presence and/or activity of said protease or its precursor after activation, wherein said target is a modified pro-caspase containing an activation site which is cleavable by a protease having said target specificity.

2. A method according to claim 1 wherein the proteolytic cleavage of said modified pro-caspase activates the pro-caspase and wherein the resulting activity of said activated pro-caspase is determined using a suitable substrate of the activated pro-caspase.

3. A method according to claim 1 wherein said sample is selected from the group consisting of a biological fluid, a fraction thereof, a biological tissue, an extract thereof, a fraction of such an extract, a culture medium conditioned by in vitro growing cells, tissues, or organisms, an extract of such a culture medium, and a. fraction of such a culture medium.

4. A method according to claim 1, wherein said protease is selected from the group ceneisting of serine proteases, cysteine proteases, aspartyl proteases and metalloproteases.

5. A method according to claim 4 wherein said protease is selected from the group consisting of aggrecanase, a disintegrin ans metalloproteinase (ADAM) TS1, ADAM TS4, tumor necrosis factor alpha converting enzyme (TACE), β-site of APP cleaving enzyme (BACE), BACE 1, RACE 2, HIV protease and hepatitis C protease.

6. A method according to claim 1 wherein said modified pro-caspase is derived from pro-caspase by removing its activation site and inserting, not necessarily on the same position, an activation site which is cleavable by the protease to be determined.

7. A method according to claim 1 wherein said modified pro-easpase is derived from pro-caspase by altering its activation site rendering it inactive for its natural substrate and inserting, not necessarily on the same position, an activation site which is cleavable by the protease to be determined.

8. A method according to claim 1 wherein said modified pro-caspase is selected from the group consisting of pro-caspase-1, pro-caspase-3, pro-caspase-7, pro-caspase-8, pro-caspase-9, and pro-caspase-10.

9. The method of claim 8 wherein said modified pro-caspase is pro-caspase-3- or pro-caspase-7 and wherein said modificaton in procaspase-3 or pro-caspase-7 is a replacement of D175 in wild-type pro-caspase-3 or D198 in wild-type pro-caspase-1 by a sequence selected from the group of sequences GSDMELPLPRNITEGEÔARGSVILTVKPIF EEF (SEQ ID NO: 1), GSPLAQAÔVRSSSRSG (SEQ ID NO: 2) and GSKTEEISEVNLÔDAEFRHDS (SEQ ID NO: 3) wherein the Ô symbol indicates the cleavage site in the physiological target.

10. A method according to claim 2, wherein the caspase substrate is a compound comprising the amino acid sequence AspGluValAsp-pNA (SEQ ID NO: 4), in which pNA is p-nitro-anilide.

11. A method according to claim 2 wherein said sample is selected from the group consisting of a biological fluid, a fraction thereof, a biological tissue, an extract thereof, a fraction of such an extract, a culture medium conditioned by in vitro growing cells, tissues, or organisms, an extract of such a culture medium, and a fraction of such a culture medium.

12. A method according to claim 11 wherein:
said protease is selected from the group consisting of serine proteases, cysteine proteases, aspartyl proteases and metalloproteases;
said modified pro-caspase is derived from a pro-caspase by replacing its activation site by an activation site which is cleavable by the protease to be determined;
said modified pro-caspase is derived from pro-caspase by removing its activation site and inserting, not necessarily on the same position, an activation site which is cleavable by the protease to be determined, said modified pro-caspase is derived from pro-caspase by altering its activation site rendering it inactive for its natural substrate and inserting, not necessarily on the same position, an activation site which is cleavable by the protease to be determined;
said modified pro-caspase is selected from the group consisting of pro-caspase-1, pro-caspase-3, pro-caspase-7, pro-caspase-8, pro-caspase-9, and pro-caspase-10;
the caspase substrate is a compound comprising the amino acid sequence AspGluValAsp-pNa (SEQ ID NO: 4), in which pNA is p-nitro-anilide.

13. A method according to claim 12 wherein said protease is selected from the group consisting of aggrecanase, a disintegrin and metalloproteinase (ADAM) TS1, ADAM TS4, tumor necrosis factor alpha converting enzyme (TACE), β-site of APP cleaving enzyme (BACE), BACE 1, BACE 2, HIV protease and hepatitis C protease.

14. A method according to claim 12 wherein said modified pro-caspase is pro-caspase-3 or pro-caspase-7 and wherein said modification in pro-caspase-3 or pro-caspase-7 is a replacement of D175 in wild-type pro-caspase-5 or D198 in wild-type pro-caspase-7 by a sequence selected from the group of sequences GSDMELPLPRNITEGE^ARGS-VILTVKPIFEEF (SEQ TD NO: 1), GSPLAQA^VRSSSR SG (SEQ ID NO: 2) and GSKTEEISEVNL^DAEFRHDS (SEQ ID NO: 3) wherein the ^ symbol indicates the cleavage site in the physiological target.

* * * * *

UNITED STATES PATENT AND TRADEMARK OFFICE
CERTIFICATE OF CORRECTION

PATENT NO. : 7,361,485 B2
APPLICATION NO. : 10/543735
DATED : April 22, 2008
INVENTOR(S) : Verheijen et al.

It is certified that error appears in the above-identified patent and that said Letters Patent is hereby corrected as shown below:

Column 5, line 34, "TNFαconverting" should read --TNFα converting--;

Column 5, line 37, "TNFαconverting" should read --TNFα converting--;

Column 5, line 51, "1M" should read --1μM--;

Column 5, line 60, "(ADANTS4)" should read --(ADAMTS4)--;

Column 6, line 64, "arid" should read --and--;

Column 7, line 13, "Shows" should read --shows--;

Column 8, line 4, "P1" should read --P1'--;

Column 11, line 44, "f or" should read --for--;

Column 57, claim 3, line 22, "a." should read --a--;

Column 57, claim 4, line 25, "ceneisting" should read --consisting--;

Column 57, claim 5, line 29, "ans" should read --and--;

Column 57, claim 5, line 31, "RACE 2," should read --BACE 2,--;

Column 57, claim 7, line 39, "pro-easpase" should read --pro-caspase--;

Column 57, claim 9, line 52, "pro-caspase-1" should read --pro-caspase-7--;

Column 57, claim 9, lines 53 and 54, "GSDMELPLPRNITEGEÔARGSVILTVKPIFEEF" should read --GSDMELPLPRNITEGE^ARGSVILTVKPIFEEF--;

Column 57, claim 9, line 54, "GSPLAQAÔVRSSSRSG" should read --GSPLAQA^VRSSSRSG--;

Column 57, claim 9, line 55, "GSKTEEISEVNLÔDAEFRHDS" should read --GSKTEEISEVNL^DAEFRHDS--;

CERTIFICATE OF CORRECTION (continued)
U.S. Pat. No. 7,361,485 B2

Column 57, claim 9, line 56, "Ôsymbol" should read --^symbol--; and

Column 58, claim 14, line 47, "TD" should read --ID--.

Signed and Sealed this

Sixteenth Day of March, 2010

David J. Kappos
*Director of the United States Patent and Trademark Office*

```
                        SEQUENCE LISTING

<160> NUMBER OF SEQ ID NOS: 98

<210> SEQ ID NO 1
<211> LENGTH: 32
<212> TYPE: PRT
<213> ORGANISM: Artificial
<220> FEATURE:
<223> OTHER INFORMATION: Aggrecanase recognition site from aggrecan

<400> SEQUENCE: 1

Gly Ser Asp Met Glu Leu Pro Leu Pro Arg Asn Ile Thr Glu Gly Glu
1               5                   10                  15

Ala Arg Gly Ser Val Ile Leu Thr Val Lys Pro Ile Phe Glu Glu Phe
            20                  25                  30

<210> SEQ ID NO 2
<211> LENGTH: 15
<212> TYPE: PRT
<213> ORGANISM: Artificial
<220> FEATURE:
<223> OTHER INFORMATION: TACE recognition site in TNF alpha

<400> SEQUENCE: 2

Gly Ser Pro Leu Ala Gln Ala Val Arg Ser Ser Ser Arg Ser Gly
1               5                   10                  15

<210> SEQ ID NO 3
<211> LENGTH: 20
<212> TYPE: PRT
<213> ORGANISM: Artificial
<220> FEATURE:
<223> OTHER INFORMATION: BACE recognition site from beta-amyloid
      precursor protein

<400> SEQUENCE: 3

Gly Ser Lys Thr Glu Glu Ile Ser Glu Val Asn Leu Asp Ala Glu Phe
1               5                   10                  15

Arg His Asp Ser
            20

<210> SEQ ID NO 4
<211> LENGTH: 4
<212> TYPE: PRT
<213> ORGANISM: Artificial
<220> FEATURE:
<223> OTHER INFORMATION: caspase substrate
```

```
<220> FEATURE:
<221> NAME/KEY: MOD_RES
<222> LOCATION: (4)..(4)
<223> OTHER INFORMATION: bound to p-nitro-anilide

<400> SEQUENCE: 4

Asp Glu Val Asp
1

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
accatcgata accagccctg g                                              21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ccgcctcgag gtcttttggc c                                              21

<210> SEQ ID NO 7
<211> LENGTH: 7
<212> TYPE: PRT
<213> ORGANISM: Artificial
<220> FEATURE:
<223> OTHER INFORMATION: prothrombin cleavage site

<400> SEQUENCE: 7

Glu Gly Arg Ile Val Glu Gly
1               5

<210> SEQ ID NO 8
<211> LENGTH: 7
<212> TYPE: PRT
<213> ORGANISM: Artificial
<220> FEATURE:
<223> OTHER INFORMATION: Pro-urokinase cleavage site

<400> SEQUENCE: 8

Arg Phe Lys Ile Ile Gly Gly
1               5

<210> SEQ ID NO 9
<211> LENGTH: 7
<212> TYPE: PRT
<213> ORGANISM: Artificial
<220> FEATURE:
<223> OTHER INFORMATION: trypsinogen cleavage site

<400> SEQUENCE: 9

Asp Asp Lys Ile Val Gly Gly
1               5

<210> SEQ ID NO 10
<211> LENGTH: 7
<212> TYPE: PRT
<213> ORGANISM: Artificial
<220> FEATURE:
```

```
<223> OTHER INFORMATION: chymotrypsinogen cleavage site

<400> SEQUENCE: 10

Leu Ser Arg Ile Val Asn Gly
1               5

<210> SEQ ID NO 11
<211> LENGTH: 7
<212> TYPE: PRT
<213> ORGANISM: Artificial
<220> FEATURE:
<223> OTHER INFORMATION: Pro-elastase cleavage site

<400> SEQUENCE: 11

Val Tyr Arg Val Val Gly Glu
1               5

<210> SEQ ID NO 12
<211> LENGTH: 7
<212> TYPE: PRT
<213> ORGANISM: Artificial
<220> FEATURE:
<223> OTHER INFORMATION: Pro-subtilisin cleavage site

<400> SEQUENCE: 12

Ala Gly Lys Ser Asn Gly Glu
1               5

<210> SEQ ID NO 13
<211> LENGTH: 7
<212> TYPE: PRT
<213> ORGANISM: Artificial
<220> FEATURE:
<223> OTHER INFORMATION: Coagulation factor V cleavage site

<400> SEQUENCE: 13

Gly Ile Arg Ser Phe Arg Phe
1               5

<210> SEQ ID NO 14
<211> LENGTH: 7
<212> TYPE: PRT
<213> ORGANISM: Artificial
<220> FEATURE:
<223> OTHER INFORMATION: Coagulation factor VII cleavage site

<400> SEQUENCE: 14

Pro Gln Arg Ile Val Gly Gly
1               5

<210> SEQ ID NO 15
<211> LENGTH: 8
<212> TYPE: PRT
<213> ORGANISM: Artificial
<220> FEATURE:
<223> OTHER INFORMATION: Coagulation factor IX cleavage site

<400> SEQUENCE: 15

Asp Phe Thr Arg Val Val Gly Gly
1               5

<210> SEQ ID NO 16
<211> LENGTH: 8
<212> TYPE: PRT
<213> ORGANISM: Artificial
<220> FEATURE:
<223> OTHER INFORMATION: Coagulation factor X cleavage site
```

```
<400> SEQUENCE: 16

Asn Leu Thr Arg Ile Val Gly Gly
1               5

<210> SEQ ID NO 17
<211> LENGTH: 8
<212> TYPE: PRT
<213> ORGANISM: Artificial
<220> FEATURE:
<223> OTHER INFORMATION: Coagulation factor XII cleavage site

<400> SEQUENCE: 17

Ser Met Thr Arg Val Val Gly Gly
1               5

<210> SEQ ID NO 18
<211> LENGTH: 8
<212> TYPE: PRT
<213> ORGANISM: Artificial
<220> FEATURE:
<223> OTHER INFORMATION: Coagulation factor XI cleavage site

<400> SEQUENCE: 18

Ile Lys Pro Arg Ile Val Gly Gly
1               5

<210> SEQ ID NO 19
<211> LENGTH: 8
<212> TYPE: PRT
<213> ORGANISM: Artificial
<220> FEATURE:
<223> OTHER INFORMATION: kallikrein cleavage site

<400> SEQUENCE: 19

Thr Ser Thr Arg Ile Val Gly Gly
1               5

<210> SEQ ID NO 20
<211> LENGTH: 7
<212> TYPE: PRT
<213> ORGANISM: Artificial
<220> FEATURE:
<223> OTHER INFORMATION: plasminogen cleavage site

<400> SEQUENCE: 20

Pro Gly Arg Val Val Gly Gly
1               5

<210> SEQ ID NO 21
<211> LENGTH: 7
<212> TYPE: PRT
<213> ORGANISM: Artificial
<220> FEATURE:
<223> OTHER INFORMATION: cathepsin G cleavage site

<400> SEQUENCE: 21

Ala Gly Glu Ile Ile Gly Gly
1               5

<210> SEQ ID NO 22
<211> LENGTH: 4
<212> TYPE: PRT
<213> ORGANISM: Artificial
<220> FEATURE:
<223> OTHER INFORMATION: preferred caspase substrate cleavage site
```

```
<400> SEQUENCE: 22

Tyr Glu Val Asp
1

<210> SEQ ID NO 23
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 23

Trp Glu His Asp
1

<210> SEQ ID NO 24
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 24

Leu Glu Val Asp
1

<210> SEQ ID NO 25
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 25

Trp Val Ala Asp
1

<210> SEQ ID NO 26
<211> LENGTH: 5
<212> TYPE: PRT
<213> ORGANISM: Artificial
<220> FEATURE:
<223> OTHER INFORMATION: preferred caspase substrate cleavage site

<400> SEQUENCE: 26

Val Asp Val Ala Asp
1               5

<210> SEQ ID NO 27
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 27

Asp Glu His Asp
1

<210> SEQ ID NO 28
<211> LENGTH: 5
<212> TYPE: PRT
<213> ORGANISM: Artificial
<220> FEATURE:
<223> OTHER INFORMATION: preferred caspase substrate cleavage site

<400> SEQUENCE: 28
```

```
Leu Asp Glu Ser Asp
1               5

<210> SEQ ID NO 29
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 29

Ile Glu Thr Asp
1

<210> SEQ ID NO 30
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 30

Asp Met Gln Cys
1

<210> SEQ ID NO 31
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 31

Leu Glu His Asp
1

<210> SEQ ID NO 32
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 32

Leu Glu Ala Asp
1

<210> SEQ ID NO 33
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 33

Val Glu Ile Asp
1

<210> SEQ ID NO 34
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 34
```

```
Val Glu His Asp
1

<210> SEQ ID NO 35
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 35

Val Lys Met Asp
1

<210> SEQ ID NO 36
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 36

Val Asn Leu Asp
1

<210> SEQ ID NO 37
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 37

Asp Glu Val Asp
1

<210> SEQ ID NO 38
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 38

Leu Glu Thr Asp
1

<210> SEQ ID NO 39
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 39

Ile Glu Ala Asp
1

<210> SEQ ID NO 40
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 40

Ala Glu Val Asp
```

-continued

```
<210> SEQ ID NO 41
<211> LENGTH: 44
<212> TYPE: DNA
<213> ORGANISM: Artificial
<220> FEATURE:
<223> OTHER INFORMATION: oligo for pro-urokinase variant PRFK-IGGG
<220> FEATURE:
<221> NAME/KEY: CDS
<222> LOCATION: (1)..(42)

<400> SEQUENCE: 41 tcg agg ccc cgc ttt aag att ggc ggg gga gaa ttc acc acc at          44
Ser Arg Pro Arg Phe Lys Ile Gly Gly Gly Glu Phe Thr Thr
1               5                   10

<210> SEQ ID NO 42
<211> LENGTH: 14
<212> TYPE: PRT
<213> ORGANISM: Artificial
<220> FEATURE:
<223> OTHER INFORMATION: Synthetic Construct

<400> SEQUENCE: 42

Ser Arg Pro Arg Phe Lys Ile Gly Gly Gly Glu Phe Thr Thr
1               5                   10

<210> SEQ ID NO 43
<211> LENGTH: 42
<212> TYPE: DNA
<213> ORGANISM: Artificial
<220> FEATURE:
<223> OTHER INFORMATION: antisense for oligo for PRFK-IGGG

<400> SEQUENCE: 43
cgatggtggt gaattctccc ccgccaatct taaagcgggg cc                      42

<210> SEQ ID NO 44
<211> LENGTH: 44
<212> TYPE: DNA
<213> ORGANISM: Artificial
<220> FEATURE:
<223> OTHER INFORMATION: Oligo for pro-urokinase variant PRFK-IAGG
<220> FEATURE:
<221> NAME/KEY: CDS
<222> LOCATION: (1)..(42)

<400> SEQUENCE: 44 tcg agg ccc cgc ttt aag att gcc ggg gga gaa ttc acc acc at          44
Ser Arg Pro Arg Phe Lys Ile Ala Gly Gly Glu Phe Thr Thr
1               5                   10

<210> SEQ ID NO 45
<211> LENGTH: 14
<212> TYPE: PRT
<213> ORGANISM: Artificial
<220> FEATURE:
<223> OTHER INFORMATION: Synthetic Construct

<400> SEQUENCE: 45

Ser Arg Pro Arg Phe Lys Ile Ala Gly Gly Glu Phe Thr Thr
1               5                   10

<210> SEQ ID NO 46
<211> LENGTH: 42
<212> TYPE: DNA
<213> ORGANISM: Artificial
```

```
<220> FEATURE:
<223> OTHER INFORMATION: antisense for oligo PRFK-IAGG

<400> SEQUENCE: 46
cgatggtggt gaattctccc ccggcaatct taaagcgggg cc                    42

<210> SEQ ID NO 47
<211> LENGTH: 44
<212> TYPE: DNA
<213> ORGANISM: Artificial
<220> FEATURE:
<223> OTHER INFORMATION: oligo for pro-urokinase variant PRFK-IEGG
<220> FEATURE:
<221> NAME/KEY: CDS
<222> LOCATION: (1)..(42)

<400> SEQUENCE: 47 tcg agg ccc cgc ttt aag att gaa ggg gga gaa ttc acc acc at        44
Ser Arg Pro Arg Phe Lys Ile Glu Gly Gly Glu Phe Thr Thr
1               5                   10

<210> SEQ ID NO 48
<211> LENGTH: 14
<212> TYPE: PRT
<213> ORGANISM: Artificial
<220> FEATURE:
<223> OTHER INFORMATION: Synthetic Construct

<400> SEQUENCE: 48

Ser Arg Pro Arg Phe Lys Ile Glu Gly Gly Glu Phe Thr Thr
1               5                   10

<210> SEQ ID NO 49
<211> LENGTH: 42
<212> TYPE: DNA
<213> ORGANISM: Artificial
<220> FEATURE:
<223> OTHER INFORMATION: antisense for oligo PRFK-IEGG

<400> SEQUENCE: 49
cgatggtggt gaattctccc ccttcaatct taaagcgggg cc                    42

<210> SEQ ID NO 50
<211> LENGTH: 44
<212> TYPE: DNA
<213> ORGANISM: Artificial
<220> FEATURE:
<223> OTHER INFORMATION: oligo for pro-urokinase variant PRFK-AIGG
<220> FEATURE:
<221> NAME/KEY: CDS
<222> LOCATION: (1)..(42)

<400> SEQUENCE: 50 tcg agg ccc cgc ttt aag gcc att ggg gga gaa ttc acc acc at        44
Ser Arg Pro Arg Phe Lys Ala Ile Gly Gly Glu Phe Thr Thr
1               5                   10

<210> SEQ ID NO 51
<211> LENGTH: 14
<212> TYPE: PRT
<213> ORGANISM: Artificial
<220> FEATURE:
<223> OTHER INFORMATION: Synthetic Construct

<400> SEQUENCE: 51

Ser Arg Pro Arg Phe Lys Ala Ile Gly Gly Glu Phe Thr Thr
1               5                   10
```

<210> SEQ ID NO 52
<211> LENGTH: 42
<212> TYPE: DNA
<213> ORGANISM: Artificial
<220> FEATURE:
<223> OTHER INFORMATION: antisense for oligo PRFK-AIGG

<400> SEQUENCE: 52
cgatggtggt gaattctccc ccaatggcct taaagcgggg cc                          42

<210> SEQ ID NO 53
<211> LENGTH: 44
<212> TYPE: DNA
<213> ORGANISM: Artificial
<220> FEATURE:
<223> OTHER INFORMATION: oligo for pro-urokinase variant PRFK-ILGG
<220> FEATURE:
<221> NAME/KEY: CDS
<222> LOCATION: (1)..(42)

<400> SEQUENCE: 53 tcg agg ccc cgc ttt aag att ctt ggg gga gaa ttc acc acc at             44
Ser Arg Pro Arg Phe Lys Ile Leu Gly Gly Glu Phe Thr Thr
 1               5                  10

<210> SEQ ID NO 54
<211> LENGTH: 14
<212> TYPE: PRT
<213> ORGANISM: Artificial
<220> FEATURE:
<223> OTHER INFORMATION: Synthetic Construct

<400> SEQUENCE: 54

Ser Arg Pro Arg Phe Lys Ile Leu Gly Gly Glu Phe Thr Thr
 1               5                  10

<210> SEQ ID NO 55
<211> LENGTH: 42
<212> TYPE: DNA
<213> ORGANISM: Artificial
<220> FEATURE:
<223> OTHER INFORMATION: antisense for oligo PRFK-ILGG

<400> SEQUENCE: 55
cgatggtggt gaattctccc ccaagaatct taaagcgggg cc                          42

<210> SEQ ID NO 56
<211> LENGTH: 44
<212> TYPE: DNA
<213> ORGANISM: Artificial
<220> FEATURE:
<223> OTHER INFORMATION: oligo for pro-urokinase variant PRFK-ILGG
<220> FEATURE:
<221> NAME/KEY: CDS
<222> LOCATION: (1)..(42)

<400> SEQUENCE: 56 tcg agg ccc cgc ttt aag ctt att ggg gga gaa ttc acc acc at             44
Ser Arg Pro Arg Phe Lys Leu Ile Gly Gly Glu Phe Thr Thr
 1               5                  10

<210> SEQ ID NO 57
<211> LENGTH: 14
<212> TYPE: PRT
<213> ORGANISM: Artificial
<220> FEATURE:
<223> OTHER INFORMATION: Synthetic Construct

```
<400> SEQUENCE: 57

Ser Arg Pro Arg Phe Lys Leu Ile Gly Gly Glu Phe Thr Thr
1               5                   10

<210> SEQ ID NO 58
<211> LENGTH: 42
<212> TYPE: DNA
<213> ORGANISM: Artificial
<220> FEATURE:
<223> OTHER INFORMATION: antisense for oligo PRFK-LIGG

<400> SEQUENCE: 58
cgatggtggt gaattctccc ccaataagct taaagcgggg cc                      42

<210> SEQ ID NO 59
<211> LENGTH: 44
<212> TYPE: DNA
<213> ORGANISM: Artificial
<220> FEATURE:
<223> OTHER INFORMATION: oligo for pro-urokinase PRFK-IVGG
<220> FEATURE:
<221> NAME/KEY: CDS
<222> LOCATION: (1)..(42)

<400> SEQUENCE: 59 tcg agg ccc cgc ttt aag att gtg ggg gga gaa ttc acc acc at         44
Ser Arg Pro Arg Phe Lys Ile Val Gly Gly Glu Phe Thr Thr
1               5                   10

<210> SEQ ID NO 60
<211> LENGTH: 14
<212> TYPE: PRT
<213> ORGANISM: Artificial
<220> FEATURE:
<223> OTHER INFORMATION: Synthetic Construct

<400> SEQUENCE: 60

Ser Arg Pro Arg Phe Lys Ile Val Gly Gly Glu Phe Thr Thr
1               5                   10

<210> SEQ ID NO 61
<211> LENGTH: 42
<212> TYPE: DNA
<213> ORGANISM: Artificial
<220> FEATURE:
<223> OTHER INFORMATION: antisense for oligo PRFK-IVGG

<400> SEQUENCE: 61
cgatggtggt gaattctccc cccacaatct taaagcgggg cc                      42

<210> SEQ ID NO 62
<211> LENGTH: 44
<212> TYPE: DNA
<213> ORGANISM: Artificial
<220> FEATURE:
<223> OTHER INFORMATION: oligo for pro-urokinase PRFK-VIGG
<220> FEATURE:
<221> NAME/KEY: CDS
<222> LOCATION: (1)..(42)

<400> SEQUENCE: 62 tcg agg ccc cgc ttt aag gtg att ggg gga gaa ttc acc acc at         44
Ser Arg Pro Arg Phe Lys Val Ile Gly Gly Glu Phe Thr Thr
1               5                   10

<210> SEQ ID NO 63
<211> LENGTH: 14
```

```
<212> TYPE: PRT
<213> ORGANISM: Artificial
<220> FEATURE:
<223> OTHER INFORMATION: Synthetic Construct

<400> SEQUENCE: 63

Ser Arg Pro Arg Phe Lys Val Ile Gly Gly Glu Phe Thr Thr
1               5                   10

<210> SEQ ID NO 64
<211> LENGTH: 42
<212> TYPE: DNA
<213> ORGANISM: Artificial
<220> FEATURE:
<223> OTHER INFORMATION: antisense for oligo PRFK-VIGG

<400> SEQUENCE: 64
cgatggtggt gaattctccc ccaatcacct taaagcgggg cc                    42

<210> SEQ ID NO 65
<211> LENGTH: 44
<212> TYPE: DNA
<213> ORGANISM: Artificial
<220> FEATURE:
<223> OTHER INFORMATION: oligo for pro-urokinase PRFK-DIGG
<220> FEATURE:
<221> NAME/KEY: CDS
<222> LOCATION: (1)..(42)

<400> SEQUENCE: 65 tcg agg ccc cgc ttt aag gat att ggg gga gaa ttc acc acc at       44
Ser Arg Pro Arg Phe Lys Asp Ile Gly Gly Glu Phe Thr Thr
1               5                   10

<210> SEQ ID NO 66
<211> LENGTH: 14
<212> TYPE: PRT
<213> ORGANISM: Artificial
<220> FEATURE:
<223> OTHER INFORMATION: Synthetic Construct

<400> SEQUENCE: 66

Ser Arg Pro Arg Phe Lys Asp Ile Gly Gly Glu Phe Thr Thr
1               5                   10

<210> SEQ ID NO 67
<211> LENGTH: 42
<212> TYPE: DNA
<213> ORGANISM: Artificial
<220> FEATURE:
<223> OTHER INFORMATION: antisense for oligo PRFK-DIGG

<400> SEQUENCE: 67
cgatggtggt gaattctccc ccattatcct taaagcgggg cc                    42

<210> SEQ ID NO 68
<211> LENGTH: 90
<212> TYPE: DNA
<213> ORGANISM: Artificial
<220> FEATURE:
<223> OTHER INFORMATION: oligo for procaspase with ADAMTS4 cleavage site
<220> FEATURE:
<221> NAME/KEY: CDS
<222> LOCATION: (6)..(89)

<400> SEQUENCE: 68 gatcc gac atg gag ctc cca ctg cct cga aac atc act gag ggt gaa gcc    50
      Asp Met Glu Leu Pro Leu Pro Arg Asn Ile Thr Glu Gly Glu Ala
```

```
                1               5                    10                  15
cga ggc agc gtg atc ctt acc gta aag ccc atc ttc gag g                         90
Arg Gly Ser Val Ile Leu Thr Val Lys Pro Ile Phe Glu
                20                   25
```

<210> SEQ ID NO 69
<211> LENGTH: 28
<212> TYPE: PRT
<213> ORGANISM: Artificial
<220> FEATURE:
<223> OTHER INFORMATION: Synthetic Construct

<400> SEQUENCE: 69

```
Asp Met Glu Leu Pro Leu Pro Arg Asn Ile Thr Glu Gly Glu Ala Arg
1               5                   10                  15

Gly Ser Val Ile Leu Thr Val Lys Pro Ile Phe Glu
                20                  25
```

<210> SEQ ID NO 70
<211> LENGTH: 90
<212> TYPE: DNA
<213> ORGANISM: Artificial
<220> FEATURE:
<223> OTHER INFORMATION: antisense for ADAMTS4-caspase

<400> SEQUENCE: 70

```
aattcctcga agatgggctt tacggtaagg atcacgctgc ctcgggcttc accctcagtg      60
atgtttcgag gcagtgggag ctccatgtcg                                      90
```

<210> SEQ ID NO 71
<211> LENGTH: 39
<212> TYPE: DNA
<213> ORGANISM: Artificial
<220> FEATURE:
<223> OTHER INFORMATION: oligo for procaspase with TACE cleavage site
<220> FEATURE:
<221> NAME/KEY: CDS
<222> LOCATION: (6)..(38)

<400> SEQUENCE: 71

```
gatcc cca ttg gca cag gca gtt aga tct tca tca cgg g                     39
      Pro Leu Ala Gln Ala Val Arg Ser Ser Ser Arg
        1               5                   10
```

<210> SEQ ID NO 72
<211> LENGTH: 11
<212> TYPE: PRT
<213> ORGANISM: Artificial
<220> FEATURE:
<223> OTHER INFORMATION: Synthetic Construct

<400> SEQUENCE: 72

```
Pro Leu Ala Gln Ala Val Arg Ser Ser Ser Arg
1               5                   10
```

<210> SEQ ID NO 73
<211> LENGTH: 39
<212> TYPE: DNA
<213> ORGANISM: Artificial
<220> FEATURE:
<223> OTHER INFORMATION: antisense for caspase-TACE

<400> SEQUENCE: 73

```
aattcccgtg atgaagatct aactgcctgt cgcaatggg                             39
```

```
<210> SEQ ID NO 74
<211> LENGTH: 60
<212> TYPE: DNA
<213> ORGANISM: Artificial
<220> FEATURE:
<223> OTHER INFORMATION: oligo for pro-caspase with BACE cleavage site
<220> FEATURE:
<221> NAME/KEY: CDS
<222> LOCATION: (6)..(59)

<400> SEQUENCE: 74 gatcc aaa aca gaa gag atc tcc gaa gtt aac ctg gac gca gag ttt cgt    50
      Lys Thr Glu Glu Ile Ser Glu Val Asn Leu Asp Ala Glu Phe Arg
      1               5                   10                  15 cat gac tca g                                                        60
His Asp Ser <210> SEQ ID NO 75
<211> LENGTH: 18
<212> TYPE: PRT
<213> ORGANISM: Artificial
<220> FEATURE:
<223> OTHER INFORMATION: Synthetic Construct

<400> SEQUENCE: 75

Lys Thr Glu Glu Ile Ser Glu Val Asn Leu Asp Ala Glu Phe Arg His
1               5                   10                  15

Asp Ser

<210> SEQ ID NO 76
<211> LENGTH: 60
<212> TYPE: DNA
<213> ORGANISM: Artificial
<220> FEATURE:
<223> OTHER INFORMATION: antisense for caspase-BACE

<400> SEQUENCE: 76
aattctgagt catgacgaaa ctctgcgtcc aggttaactt cggagatctc ttctgttttg    60

<210> SEQ ID NO 77
<211> LENGTH: 411
<212> TYPE: PRT
<213> ORGANISM: Homo sapiens
<220> FEATURE:
<221> NAME/KEY: DOMAIN
<222> LOCATION: (155)..(162)
<223> OTHER INFORMATION: urokinase cleavage site
<220> FEATURE:
<221> NAME/KEY: VARIANT
<222> LOCATION: (155)..(162)
<223> OTHER INFORMATION: TACE cleavage site: PLAQAIIGG
<220> FEATURE:
<221> NAME/KEY: VARIANT
<222> LOCATION: (155)..(162)
<223> OTHER INFORMATION: aggrecanase recognition site TEGEIIGG

<400> SEQUENCE: 77

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
```

-continued

```
                65                  70                  75                  80
Gln Gln Thr Tyr His Ala His Arg Ser Asp Ala Leu Gln Leu Gly Leu
                    85                  90                  95
Gly Lys His Asn Tyr Cys Arg Asn Pro Asp Asn Arg Arg Pro Trp
                100                 105                 110
Cys Tyr Val Gln Val Gly Leu Lys Leu Val Gln Glu Cys Met Val
                115                 120                 125
His Asp Cys Ala Asp Gly Lys Lys Pro Ser Ser Pro Pro Glu Glu Leu
    130                 135                 140
Lys Phe Gln Cys Gly Gln Lys Thr Leu Arg Pro Arg Phe Lys Ile Ile
145                 150                 155                 160
Gly Gly Glu Phe Thr Thr Ile Glu Asn Gln Pro Trp Phe Ala Ala Ile
                165                 170                 175
Tyr Arg Arg His Arg Gly Gly Ser Val Thr Tyr Val Cys Gly Gly Ser
                180                 185                 190
Leu Ile Ser Pro Cys Trp Val Ile Ser Ala Thr His Cys Phe Ile Asp
                195                 200                 205
Tyr Pro Lys Lys Glu Asp Tyr Ile Val Tyr Leu Gly Arg Ser Arg Leu
                210                 215                 220
Asn Ser Asn Thr Gln Gly Glu Met Lys Phe Glu Val Glu Asn Leu Ile
225                 230                 235                 240
Leu His Lys Asp Tyr Ser Ala Asp Thr Leu Ala His His Asn Asp Ile
                245                 250                 255
Ala Leu Leu Lys Ile Arg Ser Lys Glu Gly Arg Cys Ala Gln Pro Ser
                260                 265                 270
Arg Thr Ile Gln Thr Ile Cys Leu Pro Ser Met Tyr Asn Asp Pro Gln
                275                 280                 285
Phe Gly Thr Ser Cys Glu Ile Thr Gly Phe Gly Lys Glu Asn Ser Thr
                290                 295                 300
Asp Tyr Leu Tyr Pro Glu Gln Leu Lys Met Thr Val Val Lys Leu Ile
305                 310                 315                 320
Ser His Arg Glu Cys Gln Gln Pro His Tyr Tyr Gly Ser Glu Val Thr
                325                 330                 335
Thr Lys Met Leu Cys Ala Ala Asp Pro Gln Trp Lys Thr Asp Ser Cys
                340                 345                 350
Gln Gly Asp Ser Gly Gly Pro Leu Val Cys Ser Leu Gln Gly Arg Met
                355                 360                 365
Thr Leu Thr Gly Ile Val Ser Trp Gly Arg Gly Cys Ala Leu Lys Asp
                370                 375                 380
Lys Pro Gly Val Tyr Thr Arg Val Ser His Phe Leu Pro Trp Ile Arg
385                 390                 395                 400
Ser His Thr Lys Glu Glu Asn Gly Leu Ala Leu
                405                 410
```

<210> SEQ ID NO 78
<211> LENGTH: 93
<212> TYPE: DNA
<213> ORGANISM: Artificial
<220> FEATURE:
<223> OTHER INFORMATION: oligo for pro-urokinase with TACE cleavage site
<220> FEATURE:
<221> NAME/KEY: CDS
<222> LOCATION: (1)..(93)

<400> SEQUENCE: 78 tcc aaa ggc agc aat aag ctt ggc ccc cag agg gaa gag ttc ccc agg        48

```
Ser Lys Gly Ser Asn Lys Leu Gly Pro Gln Arg Glu Glu Phe Pro Arg
 1               5                  10                  15 gac ctc tct cta atc agc cct ctg gcc cag gca gtc att ggg gga        93
Asp Leu Ser Leu Ile Ser Pro Leu Ala Gln Ala Val Ile Gly Gly
            20                  25                  30
```

<210> SEQ ID NO 79
<211> LENGTH: 31
<212> TYPE: PRT
<213> ORGANISM: Artificial
<220> FEATURE:
<223> OTHER INFORMATION: Synthetic Construct

<400> SEQUENCE: 79

```
Ser Lys Gly Ser Asn Lys Leu Gly Pro Gln Arg Glu Glu Phe Pro Arg
 1               5                  10                  15

Asp Leu Ser Leu Ile Ser Pro Leu Ala Gln Ala Val Ile Gly Gly
            20                  25                  30
```

<210> SEQ ID NO 80
<211> LENGTH: 78
<212> TYPE: DNA
<213> ORGANISM: Artificial
<220> FEATURE:
<223> OTHER INFORMATION: oligo for pro-urokinase with aggrecan cleavage
      site
<220> FEATURE:
<221> NAME/KEY: CDS
<222> LOCATION: (1)..(78)

<400> SEQUENCE: 80

```
tcc aaa ggc aca ggt gaa gac ttt gtg gac atc cca cca ctg cct cga        48
Ser Lys Gly Thr Gly Glu Asp Phe Val Asp Ile Pro Pro Leu Pro Arg
 1               5                  10                  15 aac atc act gag ggt gaa att att ggg gga                                78
Asn Ile Thr Glu Gly Glu Ile Ile Gly Gly
            20                  25
```

<210> SEQ ID NO 81
<211> LENGTH: 26
<212> TYPE: PRT
<213> ORGANISM: Artificial
<220> FEATURE:
<223> OTHER INFORMATION: Synthetic Construct

<400> SEQUENCE: 81

```
Ser Lys Gly Thr Gly Glu Asp Phe Val Asp Ile Pro Pro Leu Pro Arg
 1               5                  10                  15

Asn Ile Thr Glu Gly Glu Ile Ile Gly Gly
            20                  25
```

<210> SEQ ID NO 82
<211> LENGTH: 4
<212> TYPE: PRT
<213> ORGANISM: Artificial
<220> FEATURE:
<223> OTHER INFORMATION: part urokinase cleavage sequence

<400> SEQUENCE: 82

```
Ile Ile Gly Gly
 1
```

<210> SEQ ID NO 83
<211> LENGTH: 4
<212> TYPE: PRT
<213> ORGANISM: Artificial

```
<220> FEATURE:
<223> OTHER INFORMATION: part urokinase cleavage sequence

<400> SEQUENCE: 83

Ile Val Gly Gly
1

<210> SEQ ID NO 84
<211> LENGTH: 4
<212> TYPE: PRT
<213> ORGANISM: Artificial
<220> FEATURE:
<223> OTHER INFORMATION: part urokinase cleavage sequence

<400> SEQUENCE: 84

Ile Ala Gly Gly
1

<210> SEQ ID NO 85
<211> LENGTH: 4
<212> TYPE: PRT
<213> ORGANISM: Artificial
<220> FEATURE:
<223> OTHER INFORMATION: part urokinase cleavage sequence

<400> SEQUENCE: 85

Ile Leu Gly Gly
1

<210> SEQ ID NO 86
<211> LENGTH: 4
<212> TYPE: PRT
<213> ORGANISM: Artificial
<220> FEATURE:
<223> OTHER INFORMATION: part urokinase cleavage sequence

<400> SEQUENCE: 86

Val Ile Gly Gly
1

<210> SEQ ID NO 87
<211> LENGTH: 4
<212> TYPE: PRT
<213> ORGANISM: Artificial
<220> FEATURE:
<223> OTHER INFORMATION: part urokinase cleavage sequence

<400> SEQUENCE: 87

Leu Ile Gly Gly
1

<210> SEQ ID NO 88
<211> LENGTH: 4
<212> TYPE: PRT
<213> ORGANISM: Artificial
<220> FEATURE:
<223> OTHER INFORMATION: part urokinase cleavage sequence

<400> SEQUENCE: 88

Ile Glu Gly Gly
1

<210> SEQ ID NO 89
<211> LENGTH: 4
<212> TYPE: PRT
<213> ORGANISM: Artificial
<220> FEATURE:
```

```
<223> OTHER INFORMATION: part urokinase cleavage sequence

<400> SEQUENCE: 89

Ile Gly Gly Gly
1

<210> SEQ ID NO 90
<211> LENGTH: 4
<212> TYPE: PRT
<213> ORGANISM: Artificial
<220> FEATURE:
<223> OTHER INFORMATION: part urokinase cleavage sequence

<400> SEQUENCE: 90

Asp Ile Gly Gly
1

<210> SEQ ID NO 91
<211> LENGTH: 4
<212> TYPE: PRT
<213> ORGANISM: Artificial
<220> FEATURE:
<223> OTHER INFORMATION: part urokinase cleavage sequence

<400> SEQUENCE: 91

Ala Ile Gly Gly
1

<210> SEQ ID NO 92
<211> LENGTH: 4
<212> TYPE: PRT
<213> ORGANISM: Artificial
<220> FEATURE:
<223> OTHER INFORMATION: part urokinase cleavage sequence

<400> SEQUENCE: 92

Val Ile Ser Ser
1

<210> SEQ ID NO 93
<211> LENGTH: 47
<212> TYPE: PRT
<213> ORGANISM: Homo sapiens
<220> FEATURE:
<221> NAME/KEY: MISC_FEATURE
<222> LOCATION: (1)..(47)
<223> OTHER INFORMATION: human caspase-3 151-197

<400> SEQUENCE: 93

Leu Thr Gly Lys Pro Lys Leu Phe Ile Ile Gln Ala Cys Arg Gly Thr
1               5                   10                  15

Glu Leu Asp Cys Gly Ile Glu Thr Asp Ser Gly Val Asp Asp Asp Met
            20                  25                  30

Ala Cys His Lys Ile Pro Val Asp Ala Asp Phe Leu Tyr Ala Tyr
        35                  40                  45

<210> SEQ ID NO 94
<211> LENGTH: 45
<212> TYPE: DNA
<213> ORGANISM: Artificial
<220> FEATURE:
<223> OTHER INFORMATION: oligo for pro-caspase-3 with cloning site for
      TACE cleavage site
<220> FEATURE:
<221> NAME/KEY: CDS
<222> LOCATION: (1)..(45)
```

```
<400> SEQUENCE: 94 ggc att gag aca gga tcc gat atc aag gaa ttc agt ggt gtt gat      45
Gly Ile Glu Thr Gly Ser Asp Ile Lys Glu Phe Ser Gly Val Asp
1               5                   10                  15

<210> SEQ ID NO 95
<211> LENGTH: 15
<212> TYPE: PRT
<213> ORGANISM: Artificial
<220> FEATURE:
<223> OTHER INFORMATION: Synthetic Construct

<400> SEQUENCE: 95

Gly Ile Glu Thr Gly Ser Asp Ile Lys Glu Phe Ser Gly Val Asp
1               5                   10                  15

<210> SEQ ID NO 96
<211> LENGTH: 69
<212> TYPE: DNA
<213> ORGANISM: Artificial
<220> FEATURE:
<223> OTHER INFORMATION: oligo for inserting TACE cleavage site into
      pro-caspase-3
<220> FEATURE:
<221> NAME/KEY: CDS
<222> LOCATION: (1)..(69)

<400> SEQUENCE: 96 ggc att gag aca gga tcc cca ttg gca cag gca gtt aga tct tca tca      48
Gly Ile Glu Thr Gly Ser Pro Leu Ala Gln Ala Val Arg Ser Ser Ser
1               5                   10                  15 cgg gaa ttc agt ggt gtt gat                                          69
Arg Glu Phe Ser Gly Val Asp
            20

<210> SEQ ID NO 97
<211> LENGTH: 23
<212> TYPE: PRT
<213> ORGANISM: Artificial
<220> FEATURE:
<223> OTHER INFORMATION: Synthetic Construct

<400> SEQUENCE: 97

Gly Ile Glu Thr Gly Ser Pro Leu Ala Gln Ala Val Arg Ser Ser Ser
1               5                   10                  15

Arg Glu Phe Ser Gly Val Asp
            20

<210> SEQ ID NO 98
<211> LENGTH: 4
<212> TYPE: PRT
<213> ORGANISM: Artificial
<220> FEATURE:
<223> OTHER INFORMATION: preferred caspase substrate cleavage site

<400> SEQUENCE: 98

Tyr Val Ala Asp
1
```